(12) United States Patent
Addison et al.

(10) Patent No.: US 9,050,043 B2
(45) Date of Patent: Jun. 9, 2015

(54) SYSTEMS AND METHODS FOR WAVELET TRANSFORM SCALE-DEPENDENT MULTIPLE-ARCHETYPING

(75) Inventors: Paul Addison, Midlothian (GB); James Ochs, Seattle, WA (US); James Watson, Fife (GB)

(73) Assignee: Nellcor Puritan Bennett Ireland, Mervue, Galway (IE)

( * ) Notice: Subject to any disclaimer, the term of this patent is extended or adjusted under 35 U.S.C. 154(b) by 752 days.

(21) Appl. No.: 12/773,056

(22) Filed: May 4, 2010

(65) Prior Publication Data

US 2011/0276275 A1    Nov. 10, 2011

(51) Int. Cl.
G06K 9/00      (2006.01)
A61B 5/1455    (2006.01)
A61B 5/00      (2006.01)

(52) U.S. Cl.
CPC ............ *A61B 5/14551* (2013.01); *A61B 5/726* (2013.01); *G06K 9/00503* (2013.01); *A61B 5/7264* (2013.01)

(58) Field of Classification Search
CPC .... A61B 5/7225; A61B 5/726; A61B 5/7275; A61B 5/7278; G06K 9/00516
USPC ........................ 702/19, 66, 179; 600/323–324
See application file for complete search history.

(56) References Cited

U.S. PATENT DOCUMENTS

| | | |
|---|---|---|
| 4,289,141 A | 9/1981 | Cormier |
| 5,439,483 A | 8/1995 | Duong-Van |
| 5,558,096 A | 9/1996 | Palatnik |
| 5,590,650 A | 1/1997 | Genova |
| 5,632,272 A | 5/1997 | Diab et al. |
| 5,778,881 A | 7/1998 | Sun et al. |
| 5,795,304 A | 8/1998 | Sun et al. |
| 5,797,840 A | 8/1998 | Akselrod et al. |
| 5,827,195 A | 10/1998 | Lander |
| 5,967,995 A | 10/1999 | Shusterman et al. |
| 6,002,952 A | 12/1999 | Diab et al. |
| 6,036,653 A | 3/2000 | Baba et al. |
| 6,094,592 A | 7/2000 | Yorkey et al. |

(Continued)

FOREIGN PATENT DOCUMENTS

| | | |
|---|---|---|
| JP | 09084776 A | 3/1997 |
| WO | WO-0077675 A1 | 12/2000 |

(Continued)

OTHER PUBLICATIONS

Donald B. Percival and Andrew T. Walden, Wavelet Methods for Time Series Analysis (WMTSA), Cambridge University Press, 2000, pp. 457-458.*

(Continued)

*Primary Examiner* — Janet Suglo
*Assistant Examiner* — Michael Dalbo
(74) *Attorney, Agent, or Firm* — Shvarts & Leiz LLP

(57) ABSTRACT

Methods and systems are disclosed for producing a plurality of archetype signals in wavelet space at a plurality of wavelet scales. A signal is transformed using a continuous wavelet transform based at least in part on a wavelet function. A scale dependent archetype transformed signal is computed based at least in part on the transformed signal and based at least in part on a natural periodicity of the wavelet function used to transform the signal. Information may be derived about the signal from the archetype transform signal, and stored in memory.

17 Claims, 14 Drawing Sheets

(56) References Cited

U.S. PATENT DOCUMENTS

| | | | |
|---|---|---|---|
| 6,095,984 | A | 8/2000 | Amano et al. |
| 6,117,075 | A | 9/2000 | Barnea |
| 6,129,675 | A | 10/2000 | Jay |
| 6,135,966 | A | 10/2000 | Ko |
| 6,171,257 | B1 | 1/2001 | Weil et al. |
| 6,171,258 | B1 | 1/2001 | Karakasoglu et al. |
| 6,208,951 | B1 | 3/2001 | Kumar et al. |
| 6,293,915 | B1 | 9/2001 | Amano et al. |
| 6,325,761 | B1 | 12/2001 | Jay |
| 6,361,501 | B1 | 3/2002 | Amano et al. |
| 6,393,311 | B1 | 5/2002 | Edgar, Jr. et al. |
| 6,561,986 | B2 | 5/2003 | Baura et al. |
| 6,608,934 | B2 | 8/2003 | Scheirer et al. |
| 6,654,623 | B1 | 11/2003 | Kästle |
| 6,810,277 | B2 | 10/2004 | Edgar, Jr. et al. |
| 6,931,269 | B2 | 8/2005 | Terry |
| 7,001,337 | B2 | 2/2006 | Dekker |
| 7,020,507 | B2 | 3/2006 | Scharf et al. |
| 7,035,679 | B2 | 4/2006 | Addison et al. |
| 7,043,293 | B1 | 5/2006 | Baura |
| 7,054,453 | B2 | 5/2006 | Causevic et al. |
| 7,054,454 | B2 | 5/2006 | Causevic et al. |
| 7,079,888 | B2 | 7/2006 | Oung et al. |
| 7,171,269 | B1* | 1/2007 | Addison et al. .............. 607/7 |
| 7,173,525 | B2 | 2/2007 | Albert |
| 7,203,267 | B2 | 4/2007 | De Man et al. |
| 7,225,013 | B2 | 5/2007 | Geva et al. |
| 7,254,500 | B2 | 8/2007 | Makeig et al. |
| 7,289,835 | B2 | 10/2007 | Mansfield et al. |
| 7,515,949 | B2 | 4/2009 | Norris |
| 7,519,488 | B2 | 4/2009 | Fu et al. |
| 7,523,011 | B2 | 4/2009 | Akiyama et al. |
| 2003/0158587 | A1* | 8/2003 | Esteller et al. .............. 607/45 |
| 2003/0163057 | A1 | 8/2003 | Flick et al. |
| 2005/0043616 | A1 | 2/2005 | Chinchoy |
| 2005/0070774 | A1* | 3/2005 | Addison et al. .............. 600/323 |
| 2006/0209631 | A1 | 9/2006 | Melese et al. |
| 2006/0211930 | A1 | 9/2006 | Scharf et al. |
| 2006/0229519 | A1 | 10/2006 | Fujiwara et al. |
| 2006/0258921 | A1* | 11/2006 | Addison et al. .............. 600/323 |
| 2006/0265022 | A1 | 11/2006 | John et al. |
| 2007/0021673 | A1 | 1/2007 | Arbel et al. |
| 2007/0073120 | A1 | 3/2007 | Li et al. |
| 2007/0073124 | A1 | 3/2007 | Li et al. |
| 2007/0167694 | A1 | 7/2007 | Causevic et al. |
| 2007/0167851 | A1 | 7/2007 | Vitali et al. |
| 2007/0282212 | A1 | 12/2007 | Sierra et al. |
| 2008/0045832 | A1 | 2/2008 | McGrath |
| 2008/0082018 | A1 | 4/2008 | Sackner et al. |
| 2008/0214903 | A1 | 9/2008 | Orbach |
| 2008/0243021 | A1 | 10/2008 | Causevic et al. |
| 2009/0082651 | A1* | 3/2009 | Baker, Jr. .............. 600/324 |
| 2009/0326402 | A1 | 12/2009 | Addison et al. |
| 2010/0087720 | A1 | 4/2010 | Addison et al. |

FOREIGN PATENT DOCUMENTS

| | | |
|---|---|---|
| WO | WO-0125802 A2 | 4/2001 |
| WO | WO-0162152 A1 | 8/2001 |
| WO | WO-03055395 A1 | 7/2003 |
| WO | WO-2004105601 A1 | 12/2004 |
| WO | WO-2005096170 A1 | 10/2005 |
| WO | WO-2006085120 A1 | 8/2006 |

OTHER PUBLICATIONS

Zheng et al., GEAIt Fault Diagnosis Based on Continuous Wavelet Transform, 2002, Mechanical Systems and Signal Processingm 16(2-3), pp. 447-457.*

Addison, Paul S., The Illustrated Wavelet Transform Handbook, Taylor & Francis Group, 2002.

Addison, Paul, "The Little Wave with the Big Future," Physics World, Mar. 2004, pp. 35-39.

Clifton et al., "Measurement of Respiratory Rate from the Photoplethysmogram in Chest Clinic Patients," Journal of Clinical Monitoring and Computing, 2006.

Leonard at al., "A Fully Automated Algorithm for the Determination of Respiratory Rate From the Photoplethysmogram," Journal of Clinical Monitoring and Computing, 2006.

Leonard et al., "An Automated Algorithm for Determining Respiratory Rate by Photoplethysmogram in Children," Acta Paediatricia, 2006; 95: 1124-1128.

Legarreta et al., "Continuous Wavelet Transform Modulus Maxima Analysis of the Electrocardiogram: Beat Characterisation and Beat-to-Beat Measurement," International Journal of Wavelets, Multiresolution and Information Processing, vol. 3, No. 1, 2004, pp. 1-24.

Yamada, Michio, "Wavelet Analysis and Its Application," Journal of the Institute of Electronics, Information and Communication Engineers, vol. 76, No. 5, May 1993, pp. 518-528.

* cited by examiner

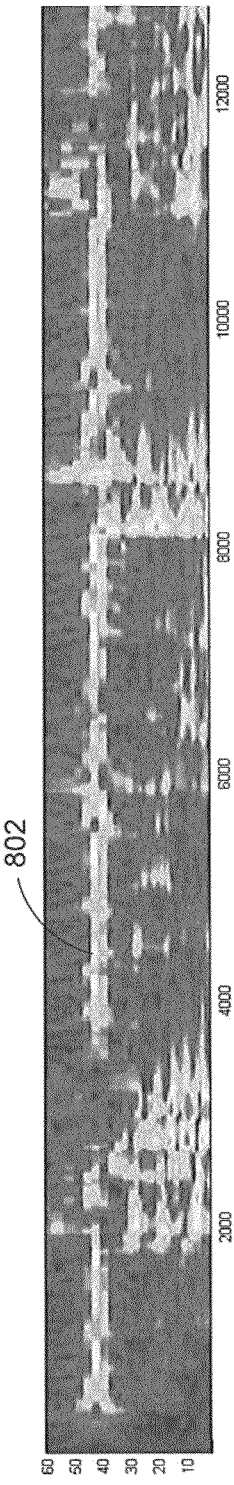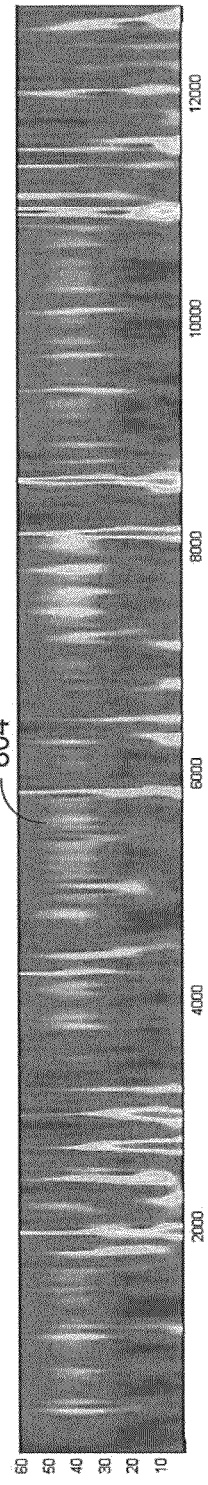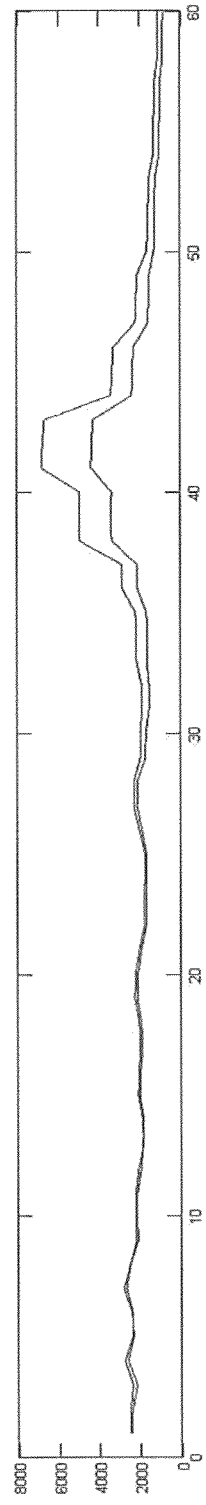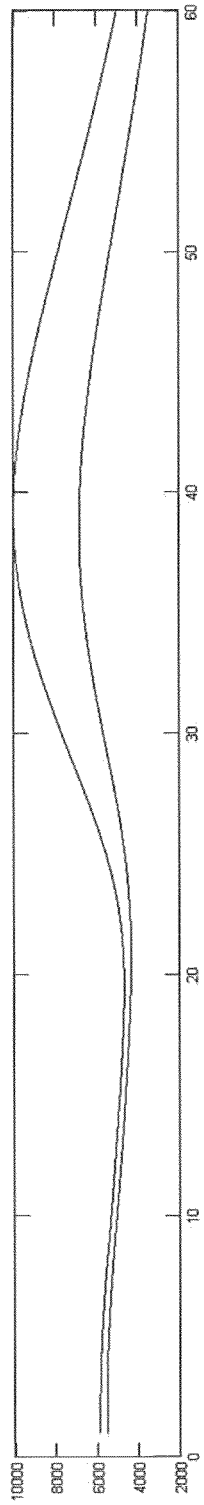

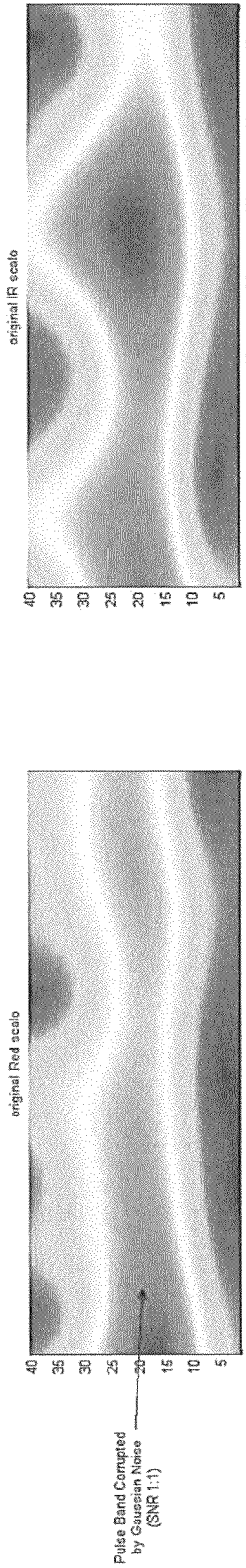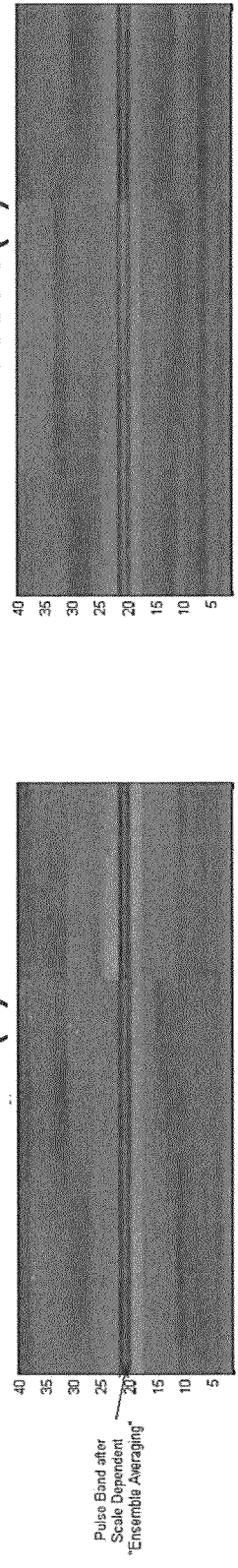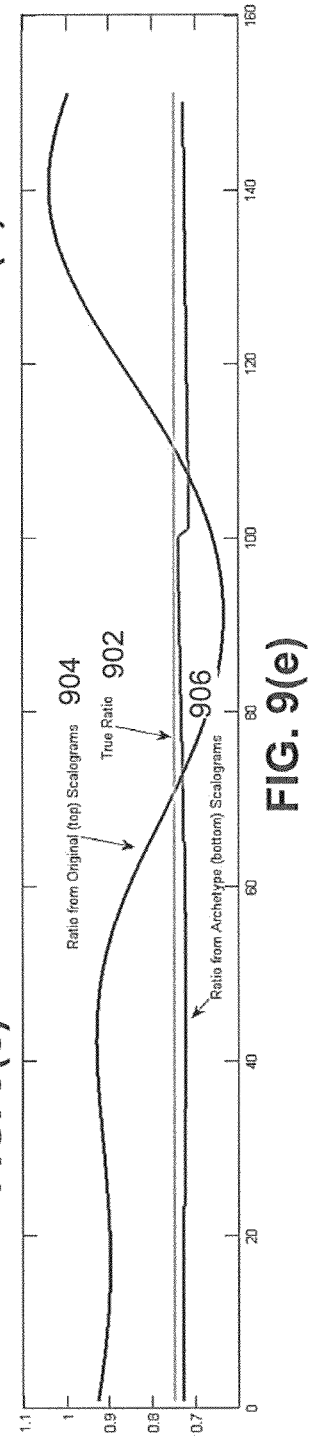

US 9,050,043 B2

SYSTEMS AND METHODS FOR WAVELET TRANSFORM SCALE-DEPENDENT MULTIPLE-ARCHETYPING

SUMMARY OF THE DISCLOSURE

The present disclosure relates to signal processing and analysis and, more particularly, the present disclosure relates to a system and method for producing a plurality of archetype signals in wavelet space at a plurality of wavelet scales for, for example, physiological signals.

Many measurement systems require one or more signal processing steps to determine useful information from a measured signal. In some applications, these signal processing steps include determining an archetype signal. In connection with deriving useful information (e.g., clinical information) from a physiological signal, an archetype wavelet transform signal, involving scale dependent signal averaging, may be derived at each scale of interest. In creating the archetype wavelet transform, the natural period of the wavelet at the scale considered may be used to determine the averaging scale. This process of creating one or more archetype wavelet transforms, as will be described in more detail below, breaks down the original signal into a number of scale-dependent archetype components, making the signal more amendable to analysis and manipulation within subsequent signal processing. Moreover, no knowledge of the underlying signal (or its periodicity) is required. In an embodiment, an archetype transform may be computed using a weighted averaging scheme.

According to one aspect, the disclosure relates to a method for processing a signal. The method includes receiving the signal. For example, the received signal may include a photoplethysmograph (PPG) signal. The method further includes using specialized processing hardware and software to transform the signal using a continuous wavelet transform to generate a transformed signal. In certain embodiments, the continuous wavelet transform is based at least in part on a wavelet function. In an embodiment, an archetype transformed signal may be computed based at least in part on the transformed signal and based at least in part on a natural periodicity of the wavelet function used to transform the signal. In an embodiment, an archetype transformed signal may be derived at each scale of interest. In an embodiment, an archetype transformed signal may be derived continuously over a range of scales.

In an embodiment, the archetype transform signal is computed using a weighted averaging scheme. The weighted averaging scheme may include at least one weight variable and a delay time. In an embodiment, the at least one weight variable may be constant or may be chosen based at least in part on a signal condition. For example, the weight variable may be chosen based at least in part on an amount of noise present in the signal, based at least in part on scale, or both. In some embodiments, the delay time may be based at least in part on the natural periodicity of the wavelet function at a scale of the wavelet function.

In an embodiment, information may be derived about the signal from the archetype transform signal, and stored in electronic memory. For example, the information may include physiological information such as pulse rate, oxygen saturation, respiration information, any other suitable physiological information, or any combination thereof. The method may further include generating an archetype scalogram based at least in part on the archetype transform signal and deriving information about the signal from the archetype scalogram. In certain embodiments, the method includes generating a first scalogram based at least in part on the transform signal.

In an embodiment, a system for processing a signal includes a receiver that receives the signal, and specialized processing hardware and software. For example, the specialized processing hardware and software may include a processor. The specialized processing hardware and software may be capable of transforming the signal using a continuous wavelet transform to generate a transformed signal. In certain embodiments, the continuous wavelet transform is based at least in part on a wavelet function. The specialized processing hardware and software may further be capable of computing an archetype transformed signal based at least in part on the transformed signal and based at least in part on a natural periodicity of the wavelet function used to transform the signal. In some embodiments, the archetype transform signal is computed using a weighted averaging scheme including at least one weight variable and a delay time. The specialized processing hardware and software may further be capable of deriving information about the signal from the archetype transform signal.

In an embodiment, the system includes a memory that stores information. The specialized processing hardware and software may further be capable of generating an archetype scalogram based at least in part on the archetype transform signal and derive information about the signal from the archetype scalogram.

BRIEF DESCRIPTION OF THE DRAWINGS

The above and other features of the present disclosure, its nature and various advantages will be more apparent upon consideration of the following detailed description, taken in conjunction with the accompanying drawings in which:

FIGS. 8(a) and 8(b) show illustrative views of a scalogram in accordance with an embodiment;

FIGS. 8(c) and 8(d) show illustrative views of summations along the time axis of the scalograms of FIGS. 8(a) and 8(b) in accordance with an embodiment.

FIGS. 9(a) and 9(b) show illustrative views of a scalogram in accordance with an embodiment;

FIGS. 9(c) and 9(d) show illustrative views of archetype scalograms in accordance with an embodiment;

FIG. 9(e) shows an illustrative view of a plot of three RITR ratios in accordance with an embodiment;

DETAILED DESCRIPTION

Figure 1:
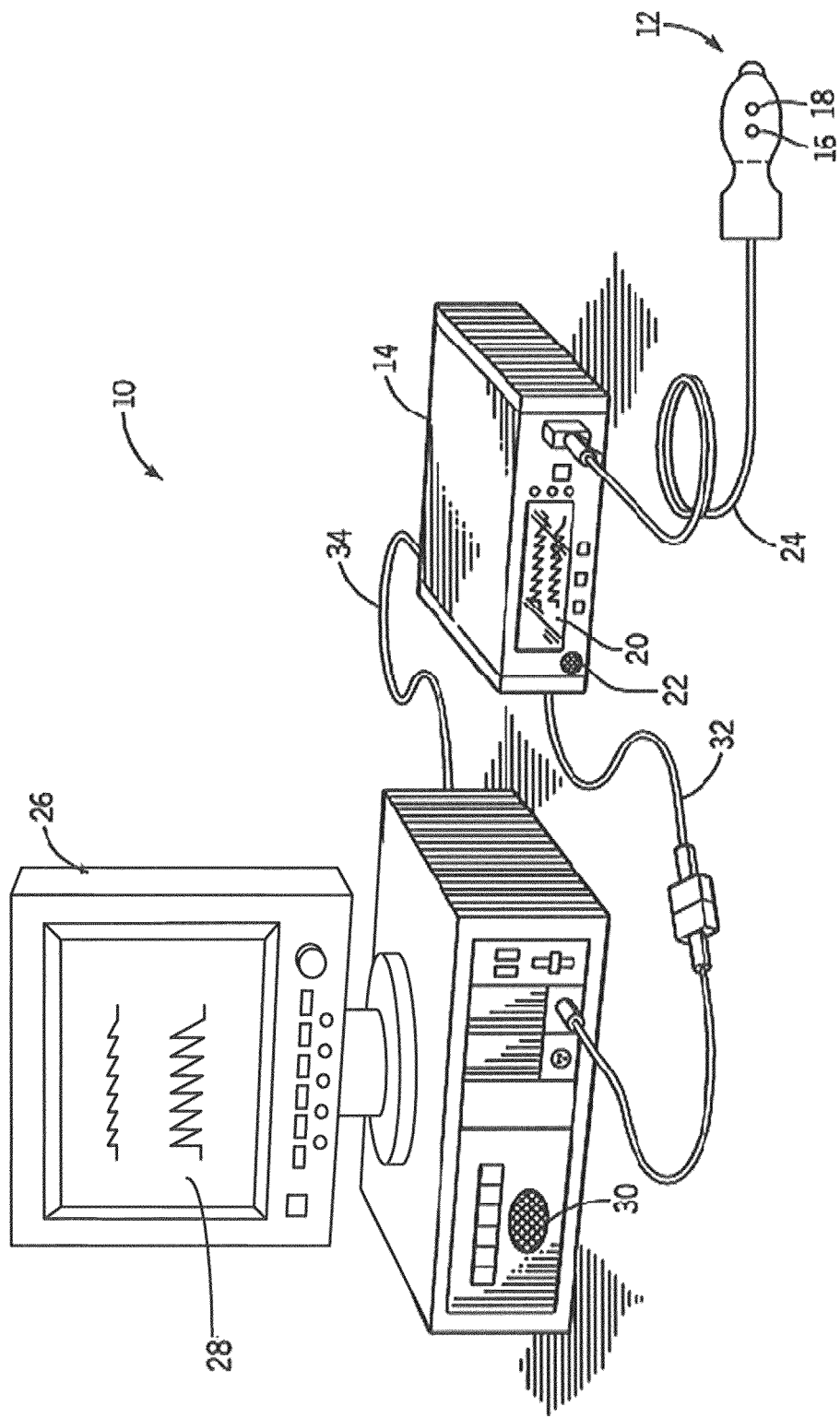
FIG. 1 shows an illustrative pulse oximetry system in accordance with an embodiment.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based on Lambert-Beer's law. The following notation will be used herein:

$$I(\lambda, t) = I_o(\lambda) \exp(-(s\beta_o(\lambda) + (1-s)\beta_r(\lambda))l(t)) \quad (1)$$

where:
$\lambda$=wavelength;
t=time;
I=intensity of light detected;
$I_o$=intensity of light transmitted;
s=oxygen saturation;
$\beta_o$, $\beta_r$=empirically derived absorption coefficients; and
l(t)=a combination of concentration and path length from emitter to detector as a function of time.

The traditional approach measures light absorption at two wavelengths (e.g., red and infrared (IR)), and then calculates saturation by solving for the "ratio of ratios" as follows.
1. First, the natural logarithm of (1) is taken ("log" will be used to represent the natural logarithm) for IR and Red $$\log I = \log I_o - (s\beta_o + (1-s)\beta_r)l \quad (2)$$

2. (2) is then differentiated with respect to time $$\frac{d\log I}{dt} = -(s\beta_o + (1-s)\beta_r)\frac{dl}{dt} \quad (3)$$

3. Red (3) is divided by IR (3)

$$\frac{d\log I(\lambda_R)/dt}{d\log I(\lambda_{IR})/dt} = \frac{s\beta_o(\lambda_R) + (1-s)\beta_r(\lambda_R)}{s\beta_o(\lambda_{IR}) + (1-s)\beta_r(\lambda_{IR})} \quad (4)$$

4. Solving for s $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR}) - \beta_r(\lambda_{IR})) - \frac{d\log I(\lambda_{IR})}{dt}(\beta_o(\lambda_R) - \beta_r(\lambda_R))}$$

Note in discrete time $$\frac{d\log I(\lambda, t)}{dt} \simeq \log I(\lambda, t_2) - \log I(\lambda, t_1)$$

Using log A−log B=log A/B, $$\frac{d\log I(\lambda, t)}{dt} \simeq \log\left(\frac{I(t_2, \lambda)}{I(t_1, \lambda)}\right)$$

So, (4) can be rewritten as $$\frac{\frac{d\log I(\lambda_R)}{dt}}{\frac{d\log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R \quad (5)$$

where R represents the "ratio of ratios." Solving (4) for s using (5) gives $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}.$$

From (5), R can be calculated using two points (e.g., PPG maximum and minimum), or a family of points. One method using a family of points uses a modified version of (5). Using the relationship $$\frac{d\log I}{dt} = \frac{dI/dt}{I} \quad (6)$$

now (5) becomes $$\frac{\frac{d\log I(\lambda_R)}{dt}}{\frac{d\log I(\lambda_{IR})}{dt}} \simeq \frac{\frac{I(t_2, \lambda_R) - I(t_1, \lambda_R)}{I(t_1, \lambda_R)}}{\frac{I(t_2, \lambda_{IR}) - I(t_1, \lambda_{IR})}{I(t_1, \lambda_{IR})}} \quad (7)$$

$$= \frac{[I(t_2, \lambda_R) - I(t_1, \lambda_R)]I(t_1, \lambda_{IR})}{[I(t_2, \lambda_{IR}) - I(t_1, \lambda_{IR})]I(t_1, \lambda_R)}$$

$$= R$$

which defines a cluster of points whose slope of y versus x will give R where $$x(t) = [I(t_2, \lambda_{IR}) - I(t_1, \lambda_{IR})]I(t_1, \lambda_R)$$

$$y(t) = [I(t_2, \lambda_R) - I(t_1, \lambda_R)]I(t_1, \lambda_{IR})$$

$$y(t) = Rx(t) \quad (8)$$

FIG. 1 is a perspective view of an embodiment of a pulse oximetry system 10. System 10 may include a sensor 12 and a pulse oximetry monitor 14. Sensor 12 may include an emitter 16 for emitting light at two or more wavelengths into a patient's tissue. A detector 18 may also be provided in sensor 12 for detecting the light originally from emitter 16 that emanates from the patient's tissue after passing through the tissue.

According to another embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as a sensor designed to obtain pulse oximetry data from a patient's forehead.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data received from sensor 12 relating to light emission and detection. In an alternative embodiment, the calculations may be performed on the monitoring device itself and the result of the oximetry reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment, sensor 12, or the sensor may, may be communicatively coupled to monitor 14 via a cable 24. However, in other embodiments, a wireless transmission device (not shown) or the like may be used instead of or in addition to cable 24.

In the illustrated embodiment, pulse oximetry system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multi-parameter patient monitor 26 may be configured to display an estimate of a patient's blood oxygen saturation generated by pulse oximetry monitor 14 (referred to as an "SpO$_2$" measurement), pulse rate information from monitor 14 and blood pressure from a blood pressure monitor (not shown) on display 28.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Figure 2:
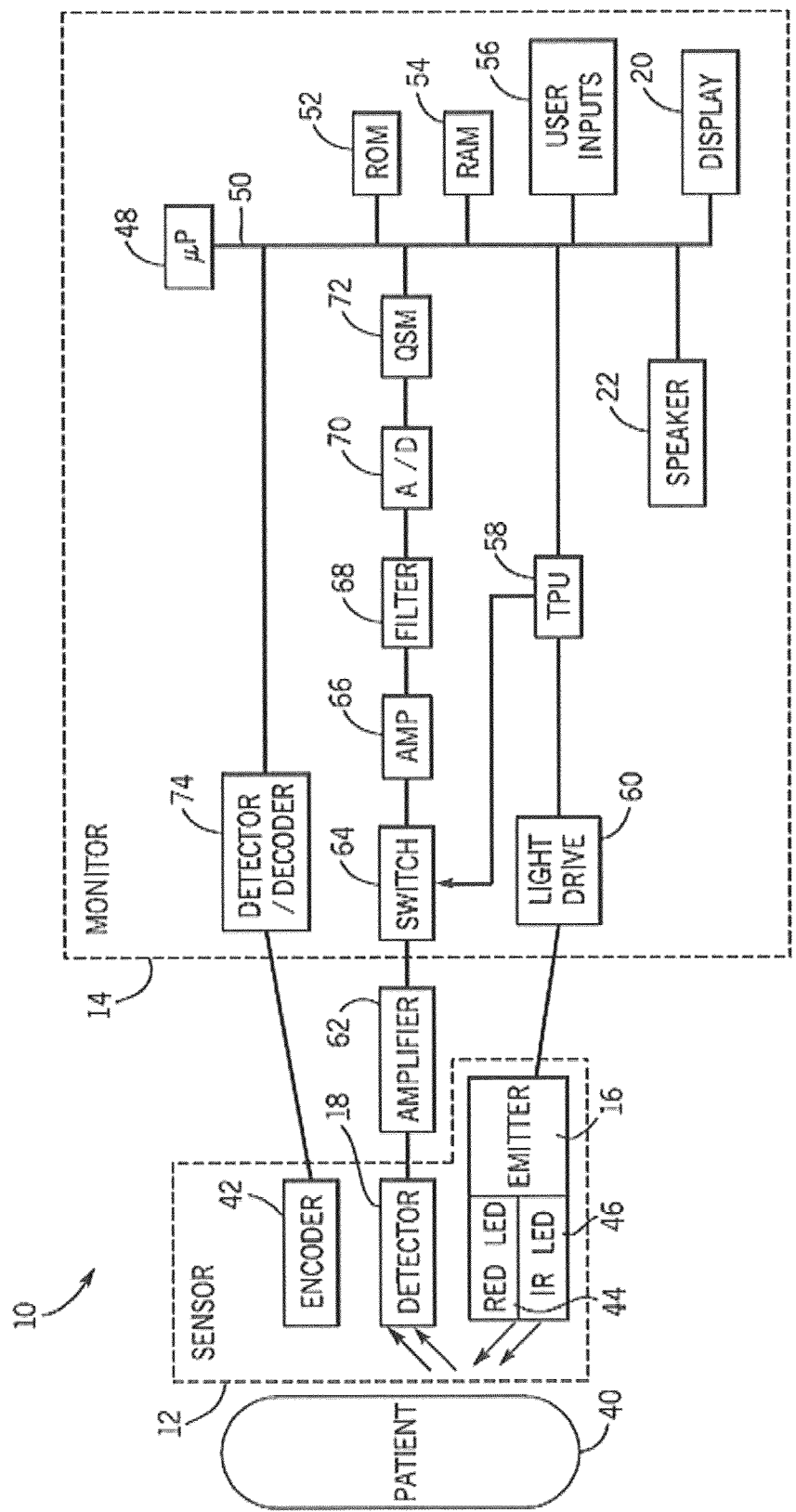
FIG. 2 is a block diagram of the illustrative pulse oximetry system of FIG. 1 coupled to a patient in accordance with an embodiment.

FIG. 2 is a block diagram of a pulse oximetry system, such as pulse oximetry system 10 of FIG. 1, which may be coupled to a patient 40 in accordance with an embodiment. Certain illustrative components of sensor 12 and monitor 14 are illustrated in FIG. 2. Sensor 12 may include emitter 16, detector 18, and encoder 42. In the embodiment shown, emitter 16 may be configured to emit at least two wavelengths of light (e.g., RED and IR) into a patient's tissue 40. Hence, emitter 16 may include a RED light emitting light source such as RED light emitting diode (LED) 44 and an IR light emitting light source such as IR LED 46 for emitting light into the patient's tissue 40 at the wavelengths used to calculate the patient's physiological parameters. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the RED and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the RED and IR wavelengths in the patient's tissue 40.

In an embodiment, encoder 42 may contain information about sensor 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the patient's physiological parameters, such as $SpO_2$ and pulse rate, using various algorithms and/or look-up tables based on the value of the received signals and/or data corresponding to the light received by detector 18. In an embodiment, microprocessor 48 may be used for signal processing. For example, microprocessor 48 may calculate an archetype transform using a weighted averaging scheme. Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the oximeter probe is attached.

Noise (e.g., from patient movement) can degrade a pulse oximetry signal relied upon by a physician, without the physician's awareness. This is especially true if the monitoring of the patient is remote, the motion is too small to be observed, or the doctor is watching the instrument or other parts of the patient, and not the sensor site. Processing pulse oximetry (i.e., PPG) signals may involve operations that reduce the amount of noise present in the signals or otherwise identify noise components in order to prevent them from affecting measurements of physiological parameters derived from the PPG signals.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In one embodiment, a PPG signal may be transformed using a continuous wavelet transform. Information derived from the transform of the PPG signal (i.e., in wavelet space) may be used to provide measurements of one or more physiological parameters.

The continuous wavelet transform of a signal x(t) in accordance with the present disclosure may be defined as $$T(a,b) = \frac{1}{\sqrt{a}} \int_{-\infty}^{+\infty} x(t)\psi*\left(\frac{t-b}{a}\right)dt \qquad (9)$$

where $\psi^*(t)$ is the complex conjugate of the wavelet function $\psi(t)$, a is the dilation parameter of the wavelet and b is the location parameter of the wavelet. The transform given by equation (9) may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain). As a further example, to reconstruct a temporal signal requires integrating twice, across time and scale, in the wavelet domain while, conversely, one integration across frequency is required to derive a temporal signal from a spectral domain. It is well known in the art that, in addition to or as an alternative to amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b)=|T(a,b)|^2 \qquad (10)$$

where '||' is the modulus operator. The scalogram may be rescaled for useful purposes. One common rescaling is defined as $$S_R(a,b) = \frac{|T(a,b)|^2}{a} \qquad (11)$$

and is useful for defining ridges in wavelet space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane are labeled a "maxima ridge".

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by $\sqrt{a}$.

In the discussion of the technology which follows herein, the "scalogram" may be taken to include all suitable forms of rescaling including, but not limited to, the original unsealed wavelet representation, linear rescaling, any power of the modulus of the wavelet transform, or any other suitable rescaling. In addition, for purposes of clarity and conciseness, the term "scalogram" shall be taken to mean the wavelet transform, T(a,b) itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The characteristic frequency associated with a wavelet of arbitrary a scale is given by $$f = \frac{f_c}{a} \quad (12)$$

where $f_c$, the characteristic frequency of the mother wavelet (i.e., at a=1), becomes a scaling constant and f is the representative or characteristic frequency for the wavelet at arbitrary scale a.

Any suitable wavelet function may be used in connection with the present disclosure. One of the most commonly used complex wavelets, the Morlet wavelet, is defined as:

$$\psi(t) = \pi^{-1/4}(e^{i2\pi f_0 t} - e^{-(2\pi f_0)^2/2})e^{-t^2/2} \quad (13)$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 \gg 0$ and can be ignored, in which case, the Morlet wavelet can be written in a simpler form as $$\psi(t) = \frac{1}{\pi^{1/4}} e^{i2\pi f_0 t} e^{-t^2/2} \quad (14)$$

This wavelet is a complex wave within a scaled Gaussian envelope. While both definitions of the Morlet wavelet are included herein, the function of equation (14) is not strictly a wavelet as it has a non-zero mean (i.e., the zero frequency term of its corresponding energy spectrum is non-zero). However, it will be recognized by those skilled in the art that equation (14) may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of PPG signals may be used to provide clinically useful information within a medical device.

Figure 3B:
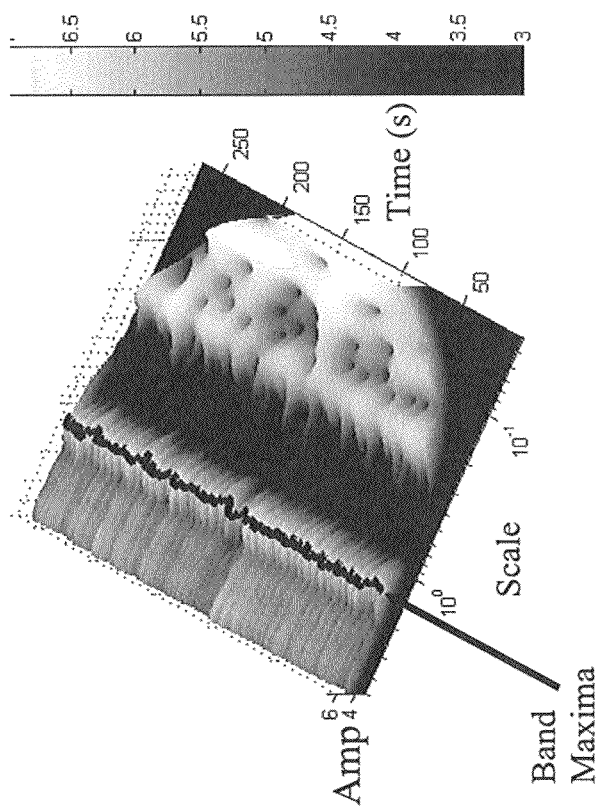
FIGS. 3(a) and 3(b) show illustrative views of a scalogram derived from a PPG signal in accordance with an embodiment.
Figure 3A:
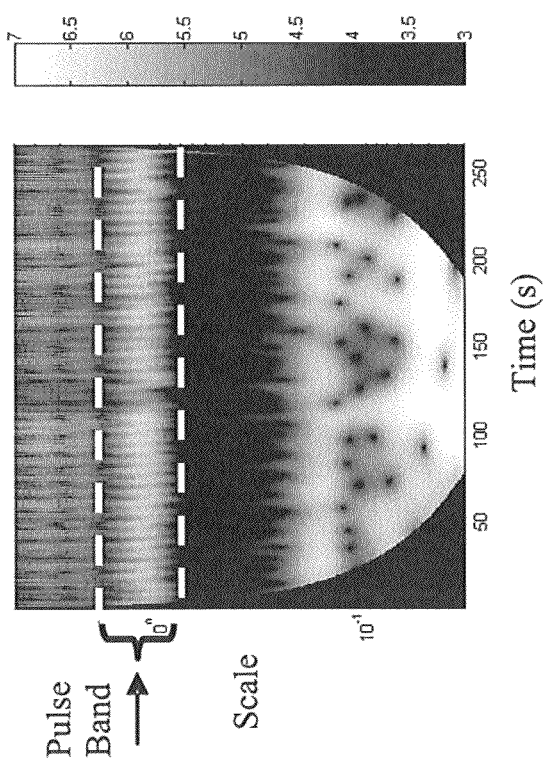

Pertinent repeating features in a signal give rise to a time-scale band in wavelet space or a rescaled wavelet space. For example, the pulse component of a PPG signal produces a dominant band in wavelet space at or around the pulse frequency. FIGS. 3(a) and (b) show two views of an illustrative scalogram derived from a PPG signal, according to an embodiment. The figures show an example of the band caused by the pulse component in such a signal. The pulse band is located between the dashed lines in the plot of FIG. 3(a). The band is formed from a series of dominant coalescing features across the scalogram. This can be clearly seen as a raised band across the transform surface in FIG. 3(b) located within the region of scales indicated by the arrow in the plot (corresponding to 60 beats per minute). The maxima of this band with respect to scale is the ridge. The locus of the ridge is shown as a black curve on top of the band in FIG. 3(b). By employing a suitable rescaling of the scalogram, such as that given in equation (11), the ridges found in wavelet space may be related to the instantaneous frequency of the signal. In this way, the pulse rate may be obtained from the PPG signal. Instead of rescaling the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 3C:
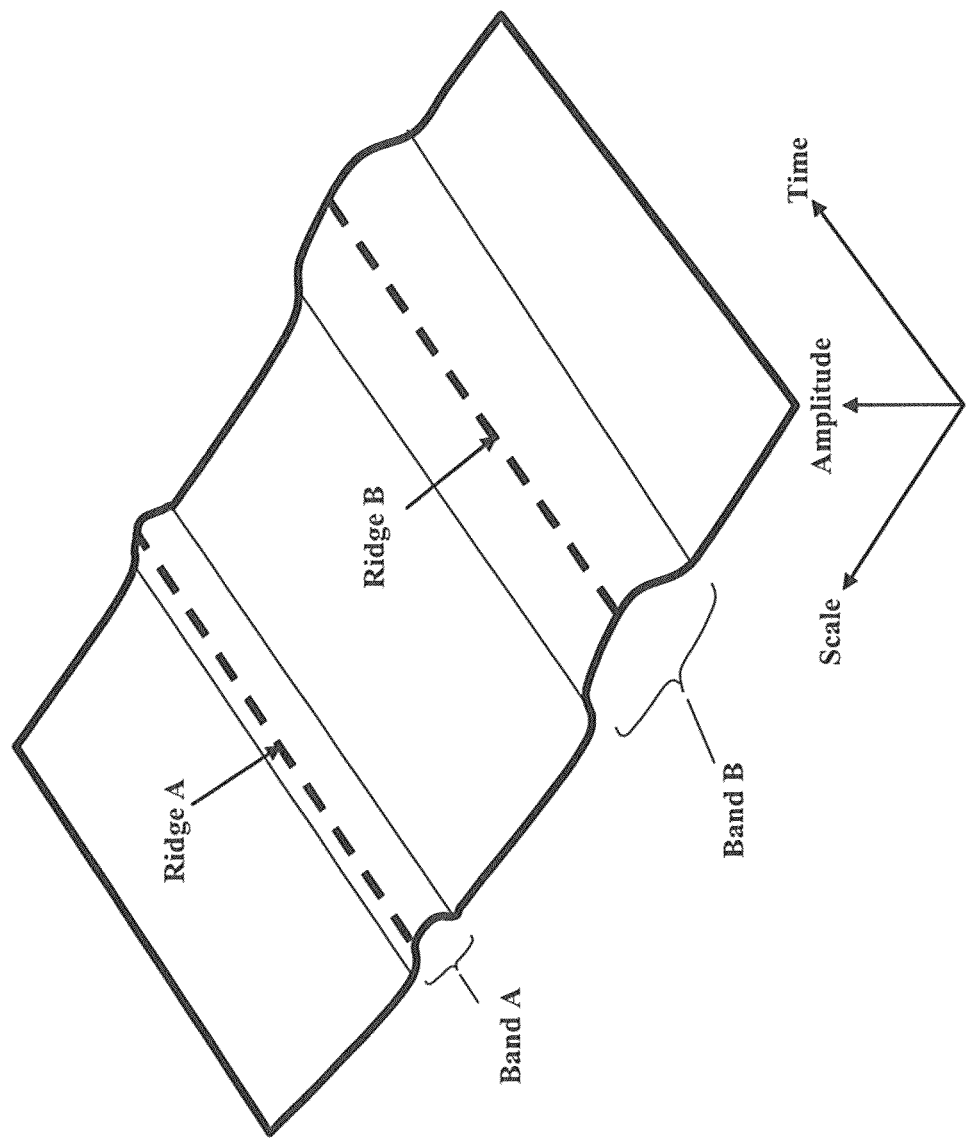
FIG. 3(c) shows an illustrative scalogram derived from a signal containing two pertinent components in accordance with an embodiment.
Figure 3D:
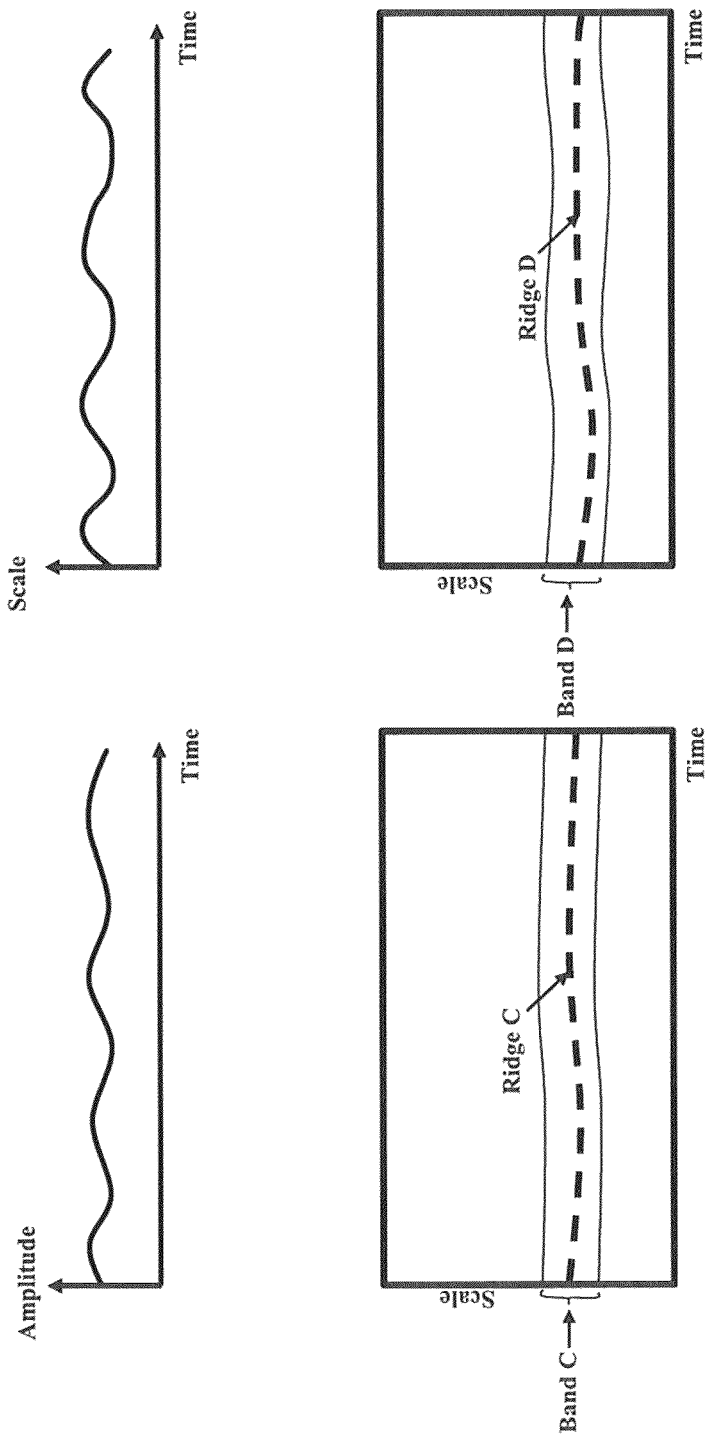
FIG. 3(d) shows an illustrative schematic of signals associated with a ridge in FIG. 3(c) and illustrative schematics of a further wavelet decomposition of these newly derived signals in accordance with an embodiment.

As discussed above, pertinent repeating features in the signal give rise to a time-scale band in wavelet space or a rescaled wavelet space. For a periodic signal, this band remains at a constant scale in the time-scale plane. For many real signals, especially biological signals, the band may be non-stationary; varying in scale, amplitude, or both over time. FIG. 3(c) shows an illustrative schematic of a wavelet transform of a signal containing two pertinent components leading to two bands in the transform space, according to an embodiment. These bands are labeled band A and band B on the three-dimensional schematic of the wavelet surface. In this embodiment, the band ridge is defined as the locus of the peak values of these bands with respect to scale. For purposes of discussion, it may be assumed that band B contains the signal information of interest. This will be referred to as the "primary band". In addition, it may be assumed that the system from which the signal originates, and from which the transform is subsequently derived, exhibits some form of coupling between the signal components in band A and band B. When noise or other erroneous features are present in the signal with similar spectral characteristics of the features of band B then the information within band B can become ambiguous (i.e., obscured, fragmented or missing). In this case, the ridge of band A may be followed in wavelet space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude or time-scale planes, respectively. The top plots of FIG. 3(d) show a schematic of the RAP and RSP signals associated with ridge A in FIG. 3(c). Below these RAP and RSP signals are schematics of a further wavelet decomposition of these newly derived signals. This secondary wavelet decomposition allows for information in the region of band B in FIG. 3(e) to be made available as band C and band D. The ridges of bands C and D may serve as instantaneous time-scale characteristic measures of the signal components causing bands C and D. This technique, which will be referred to herein as secondary wavelet feature decoupling (SWFD), may allow information concerning the nature of the signal components associated with the underlying physical process causing the primary band B (FIG. 3(e)) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts. In one embodiment, there is an inverse continuous wavelet transform which allows the original signal to be recovered from its wavelet transform by integrating over all scales and locations, a and b:

$$x(t) = \frac{1}{C_g} \int_{-\infty}^{\infty} \int_0^{\infty} T(a, b) \frac{1}{\sqrt{a}} \psi\left(\frac{t-b}{a}\right) \frac{da\,db}{a^2} \quad (15)$$

which may also be written as:

$$x(t) = \frac{1}{C_g} \int_{-\infty}^{\infty} \int_0^{\infty} T(a, b) \psi_{a,b}(t) \frac{da\,db}{a^2} \quad (16)$$

where $C_g$ is a scalar value known as the admissibility constant. It is wavelet type dependent and may be calculated from:

$$C_g = \int_0^{\infty} \frac{|\hat{\psi}(f)|^2}{f} df \quad (17)$$

Figure 3E:
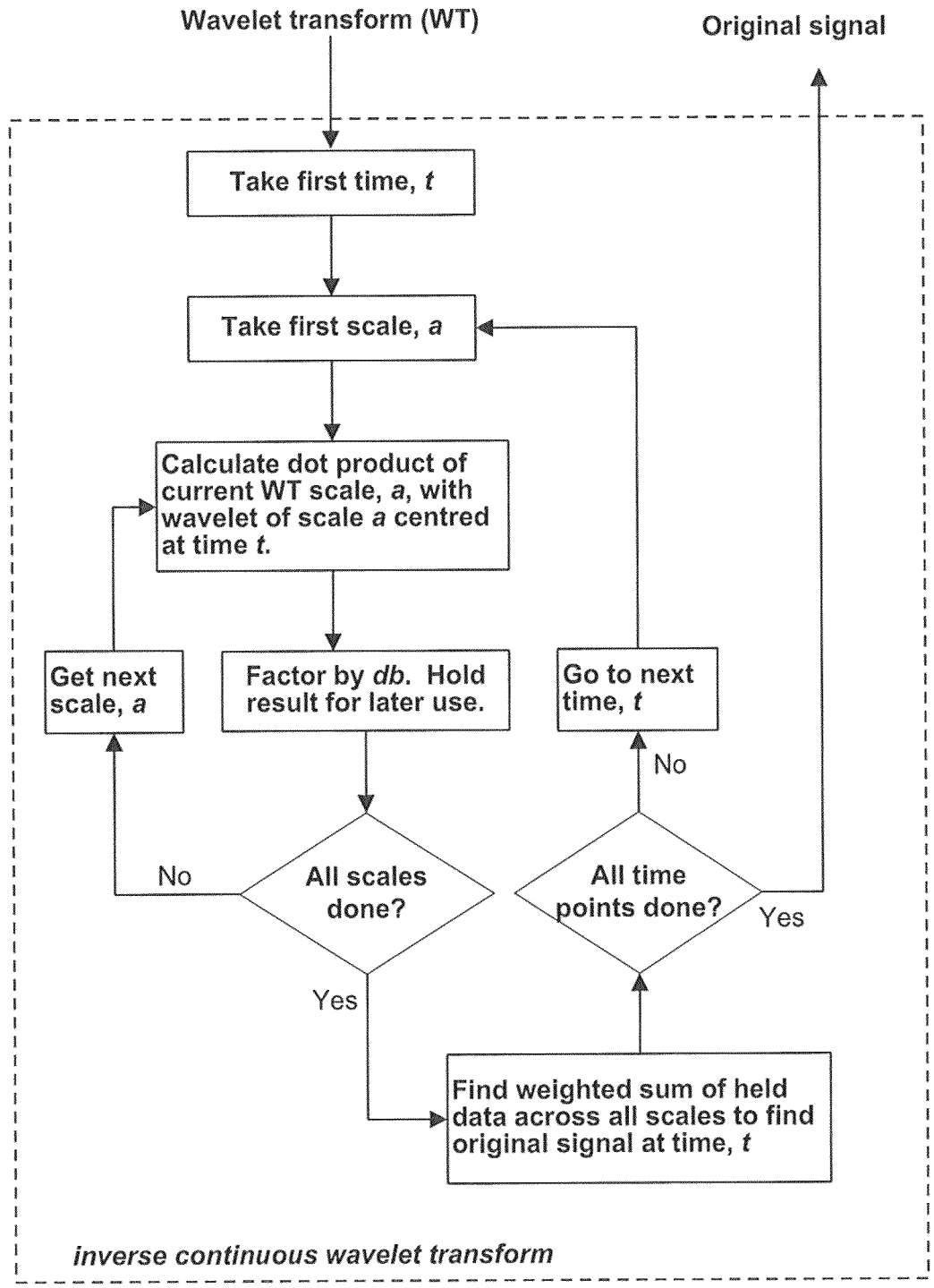
FIGS. 3(e) and 3(f) are flow charts of illustrative steps involved in performing an inverse continuous wavelet transform in accordance with embodiments.
Figure 3F:
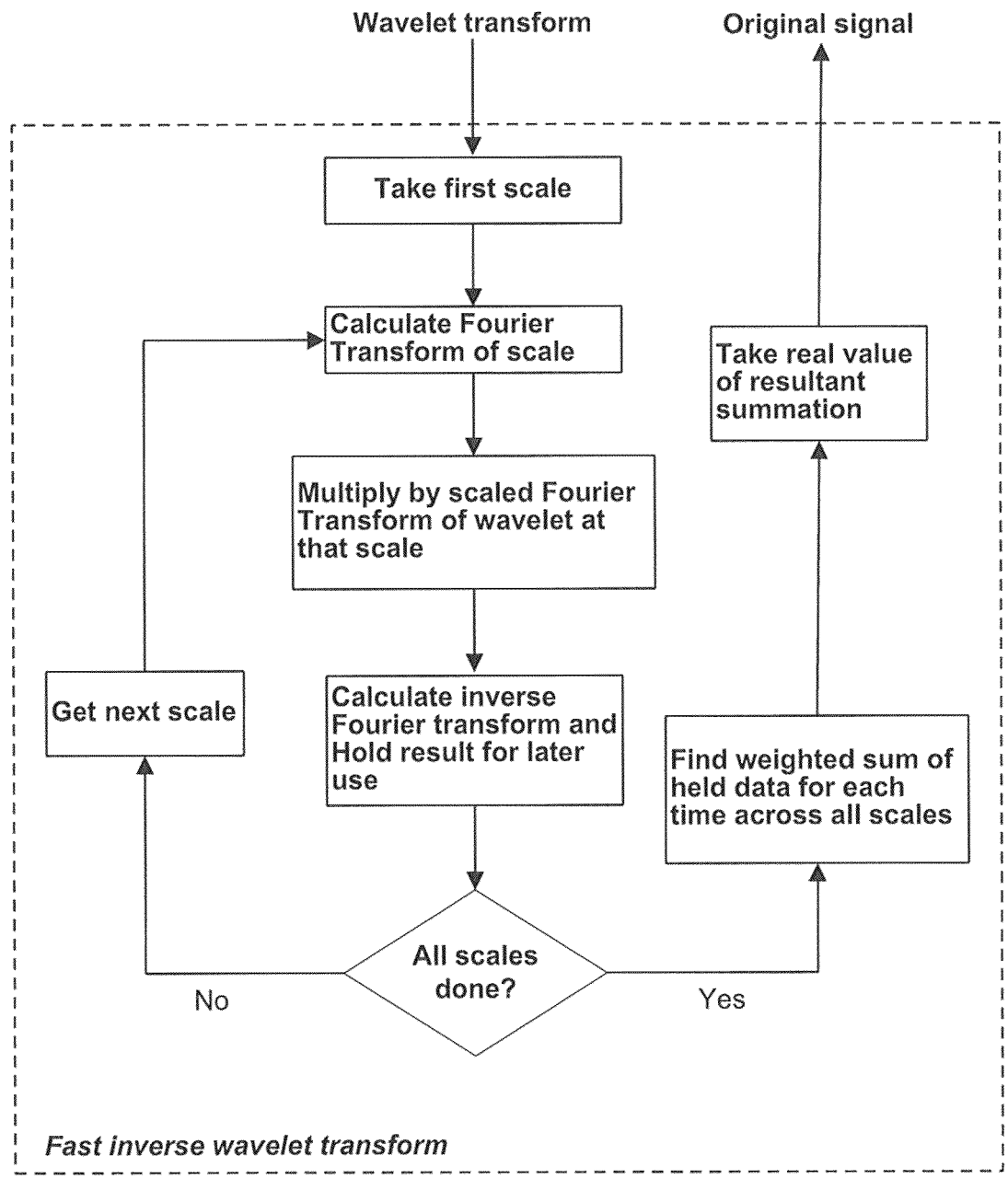

FIG. 3(e) is a flow chart of illustrative steps that may be taken to perform an inverse continuous wavelet transform in accordance with the above discussion. An approximation to the inverse transform may be made by considering equation (15) to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 3(f) is a flow chart of illustrative steps that may be taken to perform an approximation of an inverse continuous wavelet transform. It will be understood that any other suitable technique for performing an inverse continuous wavelet transform may be used in accordance with the present disclosure.

Figure 4:
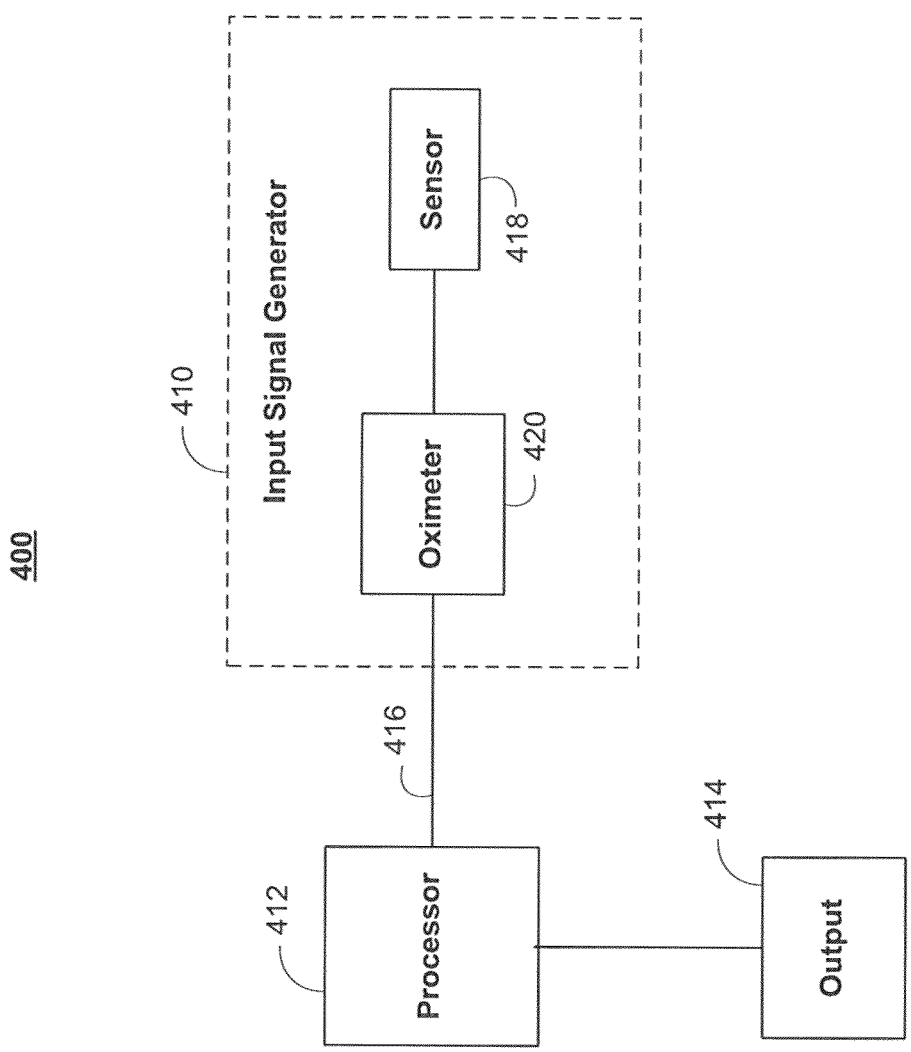
FIG. 4 is a block diagram of an illustrative continuous wavelet processing system in accordance with some embodiments.

FIG. 4 is an illustrative continuous wavelet processing system in accordance with an embodiment. In this embodiment, input signal generator 410 generates an input signal 416. As illustrated, input signal generator 410 may include oximeter 420 coupled to sensor 418, which may provide as input signal 416, a PPG signal. It will be understood that input signal generator 410 may include any suitable signal source, signal generating data, signal generating equipment, or any combination thereof to produce signal 416. Signal 416 may be any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In this embodiment, signal 416 may be coupled to processor 412. Processor 412 may be any suitable software, firmware, and/or hardware, and/or combinations thereof for processing signal 416. For example, processor 412 may include one or more hardware processors (e.g., integrated circuits), one or more software modules, computer-readable media such as memory, firmware, or any combination thereof. Processor 412 may, for example, be a computer or may be one or more chips (i.e., integrated circuits). Processor 412 may perform the calculations associated with the continuous wavelet transforms of the present disclosure as well as the calculations associated with any suitable interrogations of the transforms. Processor 412 may perform any suitable signal processing of signal 416 to filter signal 416, such as any suitable band-pass filtering, adaptive filtering, closed-loop filtering, and/or any other suitable filtering, and/or any combination thereof. Processor 416 may perform any suitable computation for signal analysis. For example, processor 416 may be capable of computing an archetype transform. In an embodiment, the archetype transform is calculated by processor 416 using a weighted averaging scheme.

Processor 412 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 412 to, for example, store data corresponding to a continuous wavelet transform of input signal 416, such as data representing a scalogram. In one embodiment, data representing a scalogram may be stored in RAM or memory internal to processor 412 as any suitable three-dimensional data structure such as a three-dimensional array that represents the scalogram as energy levels in a time-scale plane. Any other suitable data structure may be used to store data representing a scalogram.

Processor 412 may be coupled to output 414. Output 414 may be any suitable output device such as, for example, one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 400 may be incorporated into system 10 (FIGS. 1 and 2) in which, for example, input signal generator 410 may be implemented as parts of sensor 12 and monitor 14 and processor 412 may be implemented as part of monitor 14.

Figure 5:
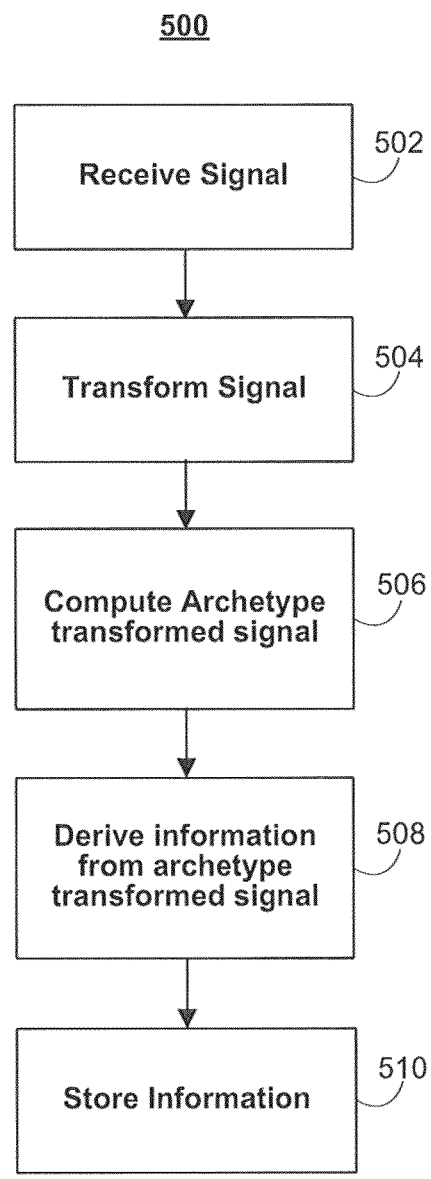
FIG. 5 is a flow chart of a method of signal processing suitable for use by the pulse oximetry systems of FIG. 1 and FIG. 2 and the continuous wavelet processing system of FIG. 4 in accordance with an embodiment.

FIG. 5 is a flow chart 500 of illustrative steps involved in determining and storing information from a computed archetype transformed signal in accordance with an embodiment. The steps of flow chart 500 may be performed by processor 412, or may be performed by any suitable processing device communicatively coupled to monitor 14. The steps of flow chart 500 may be performed by a digital processing device, or implemented in analog hardware. It will be noted that the steps of flow chart 500 may be performed in any suitable order, and certain steps may be omitted entirely.

The steps of flow chart 500 may, for example, be executed over a sliding window of a signal. For example, the steps of flow chart 500 may involve analyzing the previous N samples of a signal, or the signal received over the previous T units of time. The length of the sliding window over which the steps of flow chart 500 is executed may be fixed or dynamic. In an embodiment, the length of the sliding window may be based at least in part on the noise content of a signal. For example, the length of the sliding window may increase with increasing noise, as may be determined by a noise assessment. In an embodiment, the steps of flow chart 500 may be executed on one or more signals retrieved from memory. For example, the steps of flow chart 500 may involve analyzing one or more signals that were previously stored in ROM 52, RAM 52, and/or QSM 72 (FIG. 2(b)) in the past and may be accessed by microprocessor 48 within monitor 14 to be processed.

At step 502, at least one signal may be received. The signal (e.g., a PPG signal) may be received from any suitable source (e.g., patient 40) using any suitable technique. A received signal may be generated by sensor unit 12, which may itself include any of the number of physiological sensors described herein. A received signal may be signal 416, which may be generated by a pre-processor 420 coupled between processor 412 and sensing device 418. A received signal may include multiple signals (e.g., first and second signals), or multiple signal components. Additionally, a signal received at step 502 may be a derived signal generated internally to processor 412. Accordingly, a received signal may be based at least in part on a filtered version of a signal 416, or a combination of multiple signals. For example, a received signal may be a ratio of two signals. A received signal may be a transformation of a signal 416, such as a continuous wavelet transformation of a signal 416. A received signal may be based at least in part on past values of a signal, such as signal 416, which may be retrieved by processor 412 from a memory such as a buffer memory or RAM 54.

In an embodiment, a signal received at step 502 may be a PPG signal which may be obtained from sensor 12 that may be coupled to patient 40. A PPG signal may be obtained from input signal generator 410, which may include pre-processor 420 coupled to sensor 418, which may provide as input signal 416 a PPG signal. In an embodiment, a PPG signal may be obtained from patient 40 using sensor 12 or input signal generator 410 in real time. In an embodiment, a PPG signal may have been stored in ROM 52, RAM 52, and/or QSM 72 (FIG. 2(b)) in the past and may be accessed by microprocessor 48 within monitor 14 to be processed. One or more PPG signals may be received as input signal 416 and may include one or more of a Red PPG signal and an IR PPG signal. In an embodiment, a first signal may be a Red PPG signal, and a second signal may be an IR PPG signal. In an embodiment, a first and second signal may be different types of signals (e.g., a blood pressure signal and a pulse rate signal). In an embodiment, a first and second signal may be obtained by first and second sensors located at approximately the same body site. In an embodiment, first and second signals may be obtained by first and second sensors located at different body sites.

In an embodiment, more than two signals may be received at step 502. For example, PPG signals at three or more frequencies may be obtained at step 502. It will be noted that the steps of flow chart 500 may be applied to any number of received signals by application of the techniques described herein.

In an embodiment, one or more of the first and second signals received at step 502 may be transformed in step 504. A transformation may occur in conjunction with the receiving at step 502, or after the signals are received at step 502. In an embodiment, processor 412 may transform the signal into any suitable domain, for example, a Fourier, wavelet, spectral, scale, time, time-spectral, or any transform space. For example, a continuous wavelet transform may transform the signal into wavelet space. The continuous wavelet transform function may be based at least in part on a wavelet function, as described above. In an embodiment, the continuous wavelet transform may use a Morlet wavelet, a Mexican Hat wavelet, any other suitable wavelet, or any combination thereof. This transformation may be performed by any suitable processing device, such as processor 412 and/or microprocessor 48, which may each be a general-purpose computing device or a specialized processor. The transformation may also be performed by a separate, dedicated device. Processor 412 may further transform the original and/or transformed signals into any suitable domain. In an embodiment, a transformation may be based at least in part on a continuous wavelet transformation. For example, a PPG signal may be transformed using a continuous wavelet transform as described above with reference to FIG. 3(c). In an embodiment, a transformation may include performing a continuous wavelet transform for one or more PPG signals received, for example, at step 502, including an IR PPG signal, a Red PPG signal, or any combination of signals.

In an embodiment, a scalogram may be generated in step 504 as part of a transformation of one or more of the signals received at step 502. A scalogram may be generated by any of the techniques described herein, including those described above with reference to FIGS. 3(a) and 3(b). For example, processor 412 or microprocessor 48 may perform the calculations associated with the continuous wavelet transform of a signal and the derivation of the scalogram. In an embodiment, a scalogram may be based on any one or more features of a transformed signal. For example, a scalogram may represent the real part of a transformed signal, the imaginary part of a transformed signal, the modulus of a transformed signal, any other suitable feature of the transformed signal, or any combination thereof. In an embodiment, one or more of the signals received at step 502 may represent a scalogram of a signal. For example, a first received signal may be a continuous wavelet transformation of a Red PPG signal, and a second received signal may be a continuous wavelet transformation of an IR PPG signal.

In an embodiment, pre- or post-processing techniques may be applied to one or more of the signals received at step 502. These techniques may include any one or more of the following: compressing, multiplexing, modulating, up-sampling, down-sampling, smoothing, taking a median or other statistic of the received signal, removing erroneous regions of the received signal, or any combination thereof.

In an embodiment, the at least one signal received at step 502 may be filtered using any suitable filtering technique. For example, a signal received at sensor 12 may be filtered by a low pass filter 68 prior to undergoing additional processing at microprocessor 48 within patient monitoring system 10. The low pass filter 68 may selectively remove frequencies that may later be ignored by a transformation or other processing step, which may advantageously reduce computational time and memory requirements. In an embodiment, a signal received at step 502 may be high or band pass filtered to remove low frequencies. Such a filter may be, for example, a derivative filter. In an embodiment, a signal received at step 502 may be filtered to remove a DC component. In an embodiment, a signal received at step 502 may be normalized by dividing the signal by a DC component. In an embodiment, the cutoff frequencies of a filter may be chosen based on the frequency response of the hardware platform underlying patient monitoring system 10.

Different operations, which may include transformation, processing and/or filtering techniques, may be applied to any one or more of the signals received at step 502 and/or any components of a multi-component signal. For example, different operations may be applied to a Red PPG signal and an IR PPG signal. An operation may be applied to a portion or portions of a received signal. An operation may be broken into one or more stages performed by one or more devices within signal processing system 400 (which may itself be a part of patient monitoring system 10). For example, a filtering technique may be applied by input signal generator 410 prior to passing the resulting input signal 416 to processor 412, where it may undergo a transformation. Embodiments of the steps of flow chart 500 include any of the operations described herein performed in any suitable order.

At step 506, one or more archetype transform signals may be generated based at least in part on the transformed signal computed in step 504. An archetype transform signal may be produced at a plurality of wavelet scales. For example, an archetype transform signal component may be derived at each scale of interest. The archetype transform signal may allow for breaking down the at least one signal received at step 502 into a number of scale-dependent archetype components, thereby making the signal(s) received at step 502 more amendable to analysis and/or manipulation within subsequent signal processing. By breaking down a particular signal into archetype signals at the whole range of scales, scale dependent aspects of the signal may be partitioned from other signal components. For example, broad band noise and signal artifacts may be separated from other signal components. In an embodiment, an archetype transform signal may be based at least in part on one or more PPG signals taken from a patient. In an embodiment, an archetype transform signal may be based on a Red PPG signal and an IR PPG signal.

In an embodiment, computing the archetype transform signal includes scale dependent signal averaging whereby the natural period of the wavelet at the scale considered is used to determine the averaging scale. For example, for a Morlet wavelet, the periodicity of the internal complex oscillations within the wavelet may be taken as the inverse of the characteristic frequency of the wavelet at that scale. For the Morlet wavelet, the characteristic frequency may be taken as the dominant frequency of the wavelet function. The dominant frequency is $\omega_o/a$ radians per second, or $f_o/a$ Hertz, where $f_o=\omega_o/2\pi$. Thus, for the Morlet wavelet, the delay time 702 is $P(a)=a/f_o$. The signal averaging may be done, for example, by processor 412. The signal averaging may be performed on one or more of the transformed signals from step 504, or may be performed on the at least one signal received in step 502. By using the natural period of the wavelet at particular scale, no knowledge of the underlying signal, or its periodicity, is required to compute the archetype transform signal. For example, unlike traditional ensemble averaging techniques undertaken, for example in the time domain, there is no requirement for either a knowledge of the periodicity of the signal or a fiducial point to which the ensemble averaging should be tied (i.e. for this invention no trigger is required for the ensemble average.)

In an embodiment, generating an archetype transformed signal at step 506 may include generating one or more archetype scalograms based at least in part on the archetype transformed signal. For example, a scalogram, as described with respect to FIGS. 3(a)-3(b) may be generated based at least in part on the transformed signal computed in step 504. Generating an archetype scalogram may include determining bands of interest. For example, a band caused by the pulse component may be displayed in the archetype scalogram. In an embodiment, an archetype transform signal and/or an archetype scalogram may be displayed for a user in any manner described herein, including via displays 20 and 28.

Once an archetype transform signal is computed at step 506, information may be derived at step 508 from at least the archetype transform signal and/or the archetype scalogram. In an embodiment, the information may be physiological information derived from a comparison of oximetry signals, such as a Red PPG signal and an IR PPG signal, among other signals. The physiological information may include a physiological parameter including, but not limited to, oxygen saturation, SpO2, pulse rate, respiration rate and respiratory effort. The physiological information determined at step 508 may be quantitative or qualitative, and may be the result of applying signal processing techniques. For example, the physiological information may be at least one of an identification of a medical condition of the patient and a current physiological measurement.

In an embodiment, the information determined at step 506 may be a blood oxygen saturation measurement. The two physiological signals may be Red and IR PPG signals, transformations of Red and IR PPG signals, or features of transformations of Red and IR PPG signals, such as a ridge of a transformation. In an embodiment, a patient's blood oxygen saturation may be calculated from the determined slope by using a look-up table of slope values (stored, for example, in ROM 52). Additional blood oxygen saturation determination techniques may be applied are described in Addison et al., U.S. application Ser. No. 10/547,430, filed Feb. 27, 2004, entitled "METHOD OF ANALYZING AND PROCESSING SIGNALS," which is incorporated by reference herein in its entirety.

In an embodiment, a predictive computational model may be used to determine information at step 508. For example, a predictive computational model may determine estimates of a patient's current physiological status and prognosis as part of the determined information. A predictive computational model, executed, for example, by processor 412, may be based in part on at least one of the following data sources: the archetype transformed signal (e.g., from step 506), the transformed signal (e.g., from step 504), the received signal (e.g., input signal 416); additional signals (e.g., physiological and/or environmental signals); patient characteristics; historical data of the patient or other patients; and computational or statistical models of physiological processes. Processor 412 may retrieve any of these data sources from memory such as ROM 52 or RAM 54, from an external memory device, or from a remote memory device. The structure of a predictive computational model may, for example, be based on any of the following models: a neural network, a Bayesian classifier, and a clustering algorithm. The predictive model may also be refined based on feedback from the patient or care provider received through user inputs 56. Other predictive frameworks may include rule-based systems and adaptive rule-based systems such as propositional logic, predicate calculus, modal logic, non-monotonic logic and fuzzy logic.

At step 510, the information determined at step 508, and any other information determined during steps 502-506, may be stored to a storage device. The storage device may include any suitable storage device such as ROM 52 or RAM 54, monitor 14, processor 412, one or more remote storage devices, a physical medium such as a print-out, or any other suitable storage device known to those of skill in the art.

In an embodiment, step 510 may include outputting the information determined at step 508 to an output device. Information may be output through a graphical representation, quantitative representation, qualitative representation, or combination of representations via output 414 and may be controlled by processor 412. Output 414 may transmit physiological information by any means and through any format useful for informing a patient and a care provider of a patient status and may involve recording the physiological information to a storage medium as described above. Quantitative and/or qualitative information provided by output 414 may be displayed on a display, for example, on display 28. A graphical representation (e.g., a scalogram) may be displayed in one, two, or more dimensions and may be fixed or change with time. A graphical representation may be further enhanced by changes in color, pattern, or any other visual representation. Output 414 may communicate the information by performing at least one of the following: presenting a screen on a display; presenting a message on a display; producing a tone or sound; changing a color of a display or a light source; producing a vibration; and sending an electronic message. Output 414 may perform any of these actions in a device close to a patient, or at a mobile or remote monitoring device as described previously. In an embodiment, output 414 produces a continuous tone or beeping whose frequency changes in response to changes in a process of interest, such as a physiological process. In an embodiment, output 414 produces a colored or flashing light which changes in response to changes in a physiological process of interest.

After or during the storage of physiological information at step 510, the steps of flow chart 500 may begin again. New signals may be received, or the physiological information determination may continue on another portion of one or more of the received signal(s). In an embodiment, processor 412 may continuously or periodically perform steps 502-510 and update the information (e.g., as the patient's condition changes). The process may repeat indefinitely, until there is a command to stop the monitoring and/or until some detected event occurs that is designated to halt the monitoring process. For example, it may be desirable to halt a monitoring process when a detected noise has become too great or when at least a predetermined amount of noise has been present for a time above a predetermined threshold of time, or when a patient has undergone a change in condition that can no longer be sufficiently well-monitored in a current configuration. In an embodiment, processor 412 performs the steps of flow chart 500 at a prompt from a care provider via user inputs 56. In an embodiment, processor 412 performs the steps of flow chart 500 at intervals that may, for example, change according to patient status. For example, the steps of flow chart 500 may be performed more often when a patient is undergoing rapid changes in physiological condition, and may be performed less often as the patient's condition stabilizes.

Additional illustrative embodiments of a weighted averaging scheme for computing an archetype transformed signal will now be discussed. As described above, in an embodiment, a weighted averaging scheme used to compute one or more archetype transform signals at step 506 may include scale dependent signal averaging whereby the natural period of the wavelet at the scale considered is used to determine the averaging scale. Illustrative examples of weighted averaging computations for calculating an archetype transform signal are depicted in equations (18) and (19), and embodiments employing the archetype transform signal are discussed in detail below.

In an embodiment, the following computation may be used to find an archetype transform using a weighted averaging scheme:

$$T(a,b)' = w \cdot T(a,b) + (1-w) \cdot T(a,b-P(a))' \quad (18)$$

where w is the weight, T(a, b) is the currently computed transform value at scale a, T(a,b)' is the currently computed archetype transform value and T(a,b−P(a))' is the previous archetype value separated from the current value by a scale-dependent period P(a). In an embodiment, each time a wavelet transform value, T(a,b), is computed it is used with the previous archetype transform value T(a,b−P(a))' to form a current value of the archetype transform, T(a,b)'. At each time step in the process, an archetype wavelet transform value may be computed at each wavelet scale. In an embodiment, multiple-archetyping may be achieved by considering a range of scales.

Figure 6:
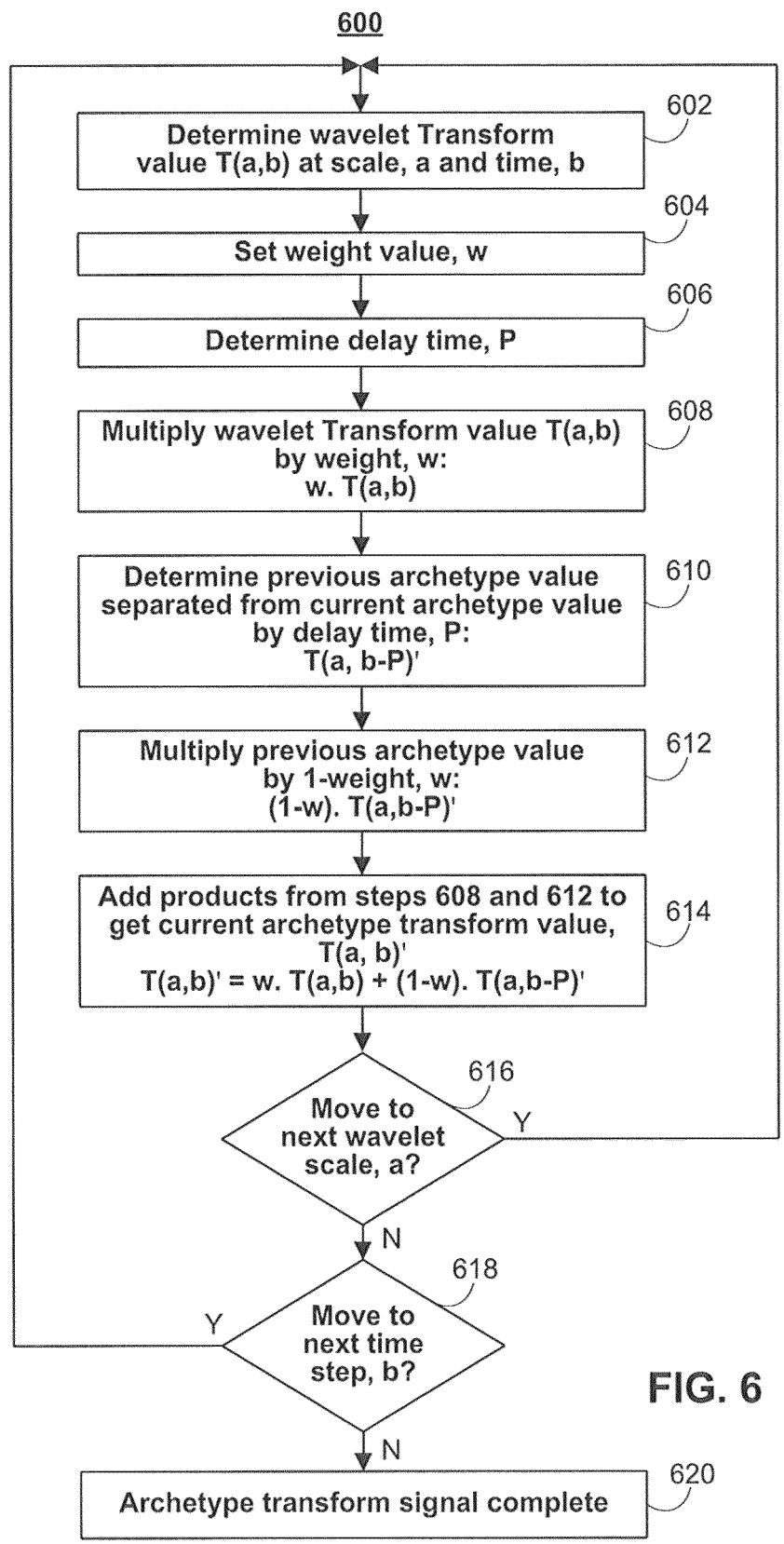
FIG. 6 is a flow chart of illustrative steps for computing an archetype transform signal in accordance with an embodiment.

FIG. 6 is a flow chart 600 of illustrative steps involved in computing an archetype transform signal using equation (18) in accordance with an embodiment. The wavelet transform value T(a,b) is determined in step 602 as a function of scale a, and time b. T(a,b) represents the currently computed transform value and may be derived from the transformed signal found in step 504 of flow chart 500. In an embodiment, scale a, and time b, may be predetermined, may represent a range of values, or may be continuously changed for analysis of a real-time signal.

In step 604, a weight value, w, is set. The weight value may be input to a patient monitoring system such as patient monitoring system 10, or may be determined automatically by the patient monitoring system 10. For example, processors 412 (FIG. 4) or 48 (FIG. 2) may calculate an appropriate weight value. The weight value may be a constant value or may be dynamically adjusted based at least in part on the signal conditions. In an embodiment, the weight value, w, may depend on a measure of noise in a signal, a measure of variability in a signal, a measure of the morphology of the signal, a measure of the intensity or relative intensity of the signal, the detection of an event in the signal, the distribution of signal energy across scales, the existence of a condition in the patient (e.g., arrhythmia), any other suitable criteria, or any combination thereof. For example, the weight value may be reduced in regions of noise. In an embodiment, if the weight value, w, is variable it may be varied according to scale, a. For example, for those scales with low noise levels, w may be set to be larger than for those scales where there is more noise.

In an embodiment, the weight value, w, may be chosen from a finite set of values. This finite set of values may represent a physiologically relevant range, and may be determined empirically and/or via predictive models. The finite set of values may be predetermined and stored, for example, in ROM 52 or RAM 54. The finite set of values may depend on one or more characteristics of the signal being analyzed or of a patient, such as a known health status. In an embodiment, the finite set of values may be based on previous determinations of physiological information. In an embodiment, the weight value may dynamically shift within the range of the finite set of values or may remain constant.

Figure 7:
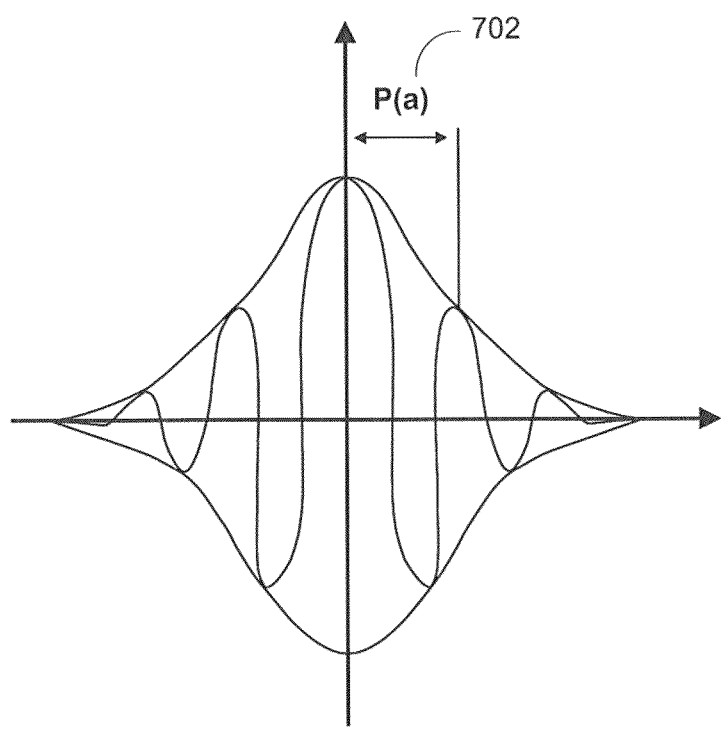
FIG. 7 is a plot of an illustrative Morlet Wavelet at scale a in accordance with an embodiment.

In step 606, a delay time, P, is determined. In an embodiment, the delay time, P, is set to the natural periodicity of the wavelet at the scale considered. However, the delay time may also be set to a predetermined constant value or determined based on other factors such as the periodicity of occurrence of a dominant signal feature (e.g. the heart beat period or respiration period), or any other suitable factor known to those of skill in the art. In the example of equation (18), the delay time, P, has been set to the natural periodicity of the wavelet at scale, a. Thus, P is a function of a. For example, for a Morlet wavelet, the periodicity may be taken as the period between oscillations within the Gaussian envelope at that scale. This is shown schematically in FIG. 7 which is an illustrative example of a plot 700 of a Morlet wavelet at scale, a, and having delay time, P(a) 702. The periodicity of the internal complex oscillations within the Morlet wavelet may be taken as the inverse of the characteristic frequency of the wavelet at that scale. As described above, for the Morlet wavelet, the characteristic frequency may be taken as the dominant frequency of the wavelet function. The dominant frequency is $\omega_o/a$ radians per second, or $f_o/a$ Hertz, where $f_o=\omega_o/2\pi$. Thus, for the Morlet wavelet, the delay time 702 is $P(a)=a/f_o$.

Once the weight value, w, and the delay time, P, have been determined, the mathematical steps of equation (18) may be carried out in steps 608-614. The wavelet transform value T(a,b) is multiplied by the weight value, w, in step 608. In step 610, T(a, b−P(a))' is computed as a function of the scale of interest, a, and the previous archetype value separated from the current value by a period P(a). In step 612, T(a, b−P(a))' is multiplied by (1−w). Finally, in step 614, the products from steps 608 and 612 may be added to get the current archetype transform value, T(a, b)'.

In step 616, it is determined whether or not to move to the next wavelet scale, a, and repeat steps 602-614. In an embodiment, steps 602-614 are repeated for each wavelet scale, a, in step 616. The range of scale values considered at step 616 may be input to a patient monitoring system such as patient monitoring system 10, or may be determined automatically by the patient monitoring system 10. For example, processors 412 (FIG. 4) or 48 (FIG. 2) may calculate an appropriate range of scales. The range of scales considered may be a constant range or may be dynamically adjusted based at least in part on the signal conditions. In an embodiment, the decision to change the scale, a, may depend on a measure of noise in a signal, a measure of variability in a signal, or any combination thereof. When the archetype transform signal has been computed for each range of scales at a particular time step in step 616, the process moves on to step 618.

In step 618, it is determined whether or not to move to the next time step, b, and repeat steps 602-616. In an embodiment, steps 602-616 are repeated for an entire time range of a given signal. The time range considered at step 618 may be input to a patient monitoring system such as patient monitoring system 10, or may be determined automatically by the patient monitoring system 10. For example, processors 412 (FIG. 4) or 48 (FIG. 2) may calculate an appropriate range of time to analyze. The range of scales considered may be a constant range or may be dynamically adjusted based at least in part on the signal conditions. In an embodiment, the time range may be continually updated for a real-time signal. For example b may range from 0 to the time point when the signal is no longer being received.

In an embodiment, equation (18) may be made continuous by considering a weighted window of points around a prior point in time. For example, the following computation may be used to find an archetype transform using a weighted averaging scheme:

$$T(a,b)'=w \cdot T(a,b)+(1-w) \cdot \int W(a,b-P(a)) \cdot T(a,b-P(a))' \, db \quad (19)$$

where W is a window which may be centered about a previous archetype value. In an embodiment, the integral of window, W, will sum to 1. Equation (19) may effectively loosen the weighted average to include points spaced by a delay approximately equal to P(a) previous to the current point rather than exactly P(a) as shown in equation (18).

When the archetype transform signal has been calculated (e.g., using equation (18) or (19)) at the desired range of scales (step 616), and the desired range of time (step 618), the archetype transform signal is completed in step 620. In an embodiment, a scalogram may be generated in step 620. A scalogram may be generated by any of the techniques described herein, including those described above with reference to FIGS. 3(a) and 3(b). For example, processor 412 or microprocessor 48 may perform the calculations associated with the archetype transform signal and the derivation of the scalogram. In an embodiment, a scalogram may be based on any one or more features of the archetype transformed signal. For example, a scalogram may represent the real part of a transformed signal, the imaginary part of a transformed signal, the modulus of a transformed signal, any other suitable feature of the transformed signal, or any combination thereof.

After or during completion of the archetype transform signal at step 620, the steps of flow chart 600 may begin again. New signals may be received, or the calculation of an archetype transform signal may continue on another portion of one or more of the received signal(s). In an embodiment, processor 412 may continuously or periodically perform steps 602-620 and update the information (e.g., as the patient's condition changes). The process may repeat indefinitely, until there is a command to stop the monitoring and/or until some detected event occurs that is designated to halt the monitoring process. In an embodiment, once the archetype transform signal has been computed, the process may move to steps 508 and 510 of flow chart 500.

In an embodiment, using the weighted average process described in flow chart 600 for computing an archetype transform signal, may allow for a running, weighted or ensemble average to be computed at each scale in the scalogram. As the dominant features, which may be a pulse band, move to other scales (e.g., due to a change in heart rate), more energy may appear at a different scale. Through the archetyping process, a new dominant archetype of the signal may be rapidly computed and displayed at the different scale.

FIGS. 8(a)-8(d) show examples of the method as described with respect to flow charts 500 and 600. FIG. 8(b) shows an illustrative example of a scalogram having pulse band 804 according to an embodiment. The scalogram of FIG. 8(b) is an example of a scalogram that may be created from a transformed signal in step 504 of FIG. 5 based on one or more signals received in step 502. FIG. 8(a) shows an illustrative example of an archetype scalogram, as may be found in step 506 according to an embodiment. The archetype scalogram of FIG. 8(a) is based at least in part on the original scalogram of FIG. 8(b) and may be calculated by the steps described in flow chart 600. The scalogram of FIG. 8(a) has pulse band 802. In an embodiment, the scalograms may be derived from the complex transform, the real part only, the imaginary part only, the modulus only, the phase only, or a combination of these realizations of the transform. In an embodiment, the scalograms shown in FIGS. 8(a) and 8(b) may be displayed on a display, for example, on display 28. The scalograms may be displayed in one, two, or more dimensions and may be fixed or change with time. The display of the scalograms may be further enhanced by changes in color, pattern, or any other visual representation.

In comparing the scalograms of FIGS. 8(a) and 8(b), pulse band 802 of the archetype scalogram is much more defined than that of pulse band 804 of the original scalogram. By computing the archetype transform signal using an ensemble averaging technique which is forced to occur at the underlying periodicity of the wavelet function (as described above), it is possible to obtain a much clearer band of interest in the scalogram than when only using transformed signal.

FIGS. 8(c) and 8(d) show illustrative plots of the summations of the archetype scalogram of FIG. 8(a) and the original scalogram of FIG. 8(b), respectively, according to an embodiment. The peak in the summation plot of FIG. 8(c) corresponds to pulse band 802 of FIG. 8(a). Similarly, the peak in the summation plot of FIG. 8(d) corresponds to pulse band 804 of FIG. 8(b). As shown in the plots, the location of the peak of the archetype scalogram summation (FIG. 8(c)) is much more defined than for the summation along the original scalogram (FIG. 8(d)). The contrast between FIGS. 8(c) and 8(d) is an example of how breaking down the original signal into a number of scale-dependent archetype components, for example through steps 602-620 of FIG. 6, may make the signal more amenable to analysis or manipulation within subsequent signal processing.

FIGS. 9(a)-9(e) show examples of how the method as described with respect to flow charts 500 and 600 may relate to pulse oximetry according to an embodiment. In an embodiment, noise may be characterized by analyzing a representation of the signal in another domain. For example, a wavelet transformation may be applied to a time domain signal to generate a scalogram as described above. Noise characteristics may be determined by analyzing the scalogram representation of a signal. The amount of useful information about the physiological process of interest may vary between different regions in a scalogram. Certain types of noise and artifact may influence certain regions more than others, with such interference often reducing the amount of useful information that can be obtained from the region. For example, patient movement may distort the scale bands associated with lower scales, while certain types of hardware noise may distort the scale bands associated with higher scales. Assessing an amount of noise may involve detecting a characteristic scalogram feature, such as a feature corresponding to the noise signature of a hardware device in the environment. Assessing an amount of noise may involve detecting an abnormality in features of the scalogram, such as those that arise in a PPG scalogram during patient movement. The amount of noise may be assessed by a quantitative or qualitative assessment.

In an embodiment, noise may be characterized by calculating an archetype transform signal to determine noise characteristics. FIGS. 9(a) and 9(b) are illustrative scalograms representing two simulated PPG signals with a R/IR ratio of 0.75. Both signals were corrupted with Gaussian noise at a Signal-to-noise ratio of 1:1. For example, FIG. 9(a) shows the scalogram for a corrupted red signal and FIG. 9(b) shows the scalogram for a corrupted IR signal. The method described in flow charts 500 and 600 may then be applied to each of the scalograms in FIGS. 9(a) and 9(b) resulting in the archetype scalograms shown in FIGS. 9(c) and 9(d), respectively. In an embodiment, the averaging periods P(a) used to obtain the scalograms in FIGS. 9(c) and 9(d), may be set to the period of the underlying wavelet at each scale a. FIG. 9(e) shows an illustrative view of a plot of three R/IR ratios in accordance with an embodiment. Curve 902 represents the true R/IR ratio (0.75), curve 904 represents the R/IR ratio taken from the original scalogram of FIGS. 9(a) and 9(b), and curve 906 represents the R/IR ratio taken from the archetype scalograms of FIGS. 9(c) and 9(d). As shown in the plot in FIG. 9(e), the ratio error is significantly reduced between the true ratio and the ratio from the archetype scalogram when compared to ratio from the original scalogram. In an embodiment, error based on noise may be identified and significantly reduced by calculating an archetype transform signal.

In an embodiment, once a noise characteristic is determined, for example at step 508, the noise characteristic may be compared to a set of noise criteria. The set of noise criteria may include one or more criteria against which a noise characteristic may be compared in order to determine which of a plurality of regression analyses to perform in subsequent steps. Noise criteria may include, but are not limited to: a noise magnitude threshold, a noise frequency range, a noise duration threshold, a noise type category, a noise source category, a noise distribution category, or any combination thereof.

Figure 10A:
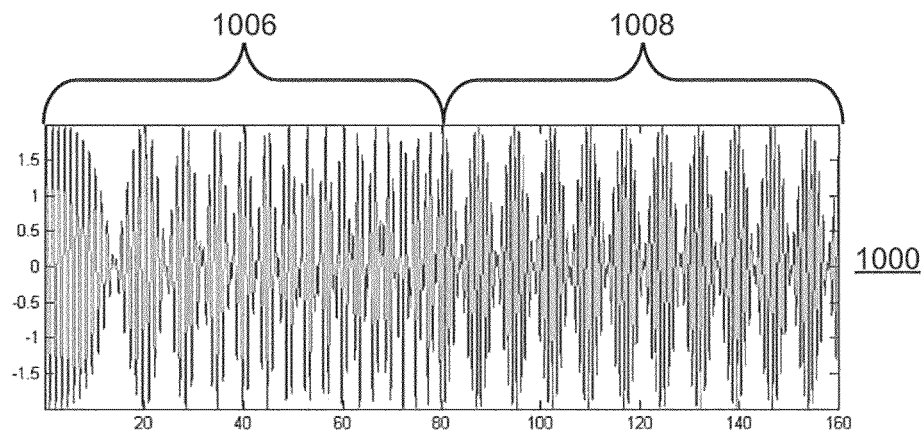
FIG. 10(a) shows an illustrative view of a plot of an original transform modulus of a test signal in accordance with an embodiment.
Figure 10B:
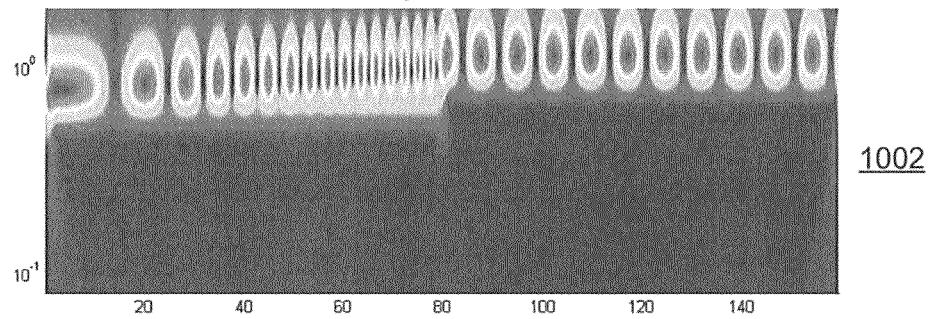
FIG. 10(b) shows an illustrative view of a wavelet transform of the test signal of FIG. 10A in accordance with an embodiment.
Figure 10C:
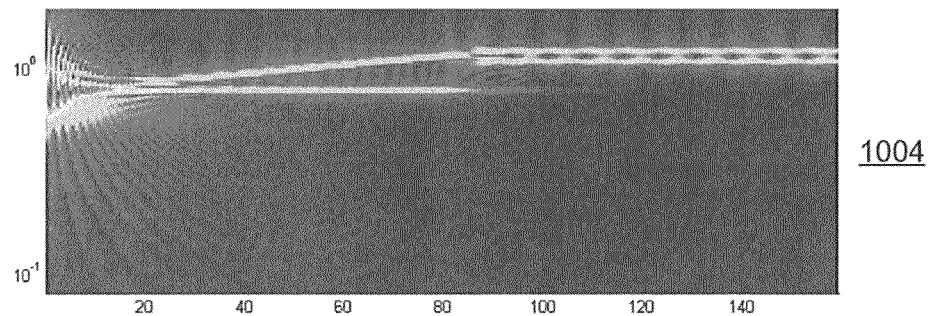
FIG. 10(c) shows an illustrative view of an archetype transform in accordance with an embodiment.

FIGS. 10(a)-10(c) show an example of how computing an archetype transform signal may contribute to discriminating between signals of differing frequencies according to an embodiment. For example, sources of noise and artifact may be discriminated from sources of interest. FIG. 10(a) shows an illustrative view of a plot 1000 of an original transform modulus of a test signal in accordance with an embodiment. The test signal is split into two halves 1006 and 1008. The first half 1006 includes two sinusoidal signals where one varies in frequency over time. The second half 1008 includes two sinusoidal signals which are very close in frequency. FIG. 10(b) shows an illustrative view of a wavelet transform scalogram 1002 of the test signal 1000 of FIG. 10A in accordance with an embodiment. As shown, the original wavelet transform scalogram 1002 does not discriminate between the combined components of the test signal 1000. Additionally, the wavelet transform scalogram 1002 exhibits broken banding. FIG. 10(c) shows an illustrative view of an archetype transform scalogram 1004 in accordance with an embodiment. The archetype transform scalogram 1004 is able to discriminate between the individual sinusoidal components of the test signal 1000.

In an embodiment, each of FIGS. 8-10 may be displayed on a display, for example, on display 28. The scalograms may be displayed in one, two, or more dimensions and may be fixed or change with time. The display of the scalograms may be further enhanced by changes in color, pattern, or any other visual representation.

It will be understood by those of skill in the art that calculating an archetype transform signal may involve methods other than that given by equations (18) and (19) and the steps given in flow charts 500 and 600. For example, other forms of averaging and weighting may be used. Additionally, the systems and methods described herein may be used with other transformation and other realization of signals at multiple scales where an intrinsic period or periods may be determined.

It will be understood that the systems and methods described herein include any combination of the above-described embodiments, as well as any combination of the noise characteristics and noise criteria described above. Additionally, the systems and methods described herein (e.g., systems for implementing the steps illustrated in one or more of flow charts 500 and 700) may be applied to time domain signals, wavelet domain signals, signals in any suitable domain, or any combination thereof. It will also be understood that the above method may be implemented using any human-readable or machine-readable instructions on any suitable system or apparatus, such as those described herein.

The foregoing is merely illustrative of the principles of this disclosure and various modifications can be made by those skilled in the art without departing from the scope and spirit of the disclosure. The following claims may also describe various aspects of this disclosure.

What is claimed is:

1. A method for processing a signal, comprising:
using a pulse oximetry system, comprising a sensor and specialized hardware and software, to perform operations comprising:
generating a photoplethysmograph (PPG) signal from the sensor, which comprises at least one emitter and at least one detector; and
using the specialized processing hardware and software for:
transforming the PPG signal using a continuous wavelet transform to generate a transformed signal, wherein the continuous wavelet transform is based at least in part on a wavelet function;
computing an archetype transformed signal by averaging the transformed signal, wherein the averaging comprises averaging points of the transformed signal with points spaced apart in time, and wherein the spacing is set to correspond to the natural period of the wavelet function used to generate the points of the transformed signal;
deriving a physiological parameter of a subject from the archetype transform signal;
storing the physiological parameter in electronic memory; and
displaying the physiological parameter using a display.

2. The method of claim 1, wherein the archetype transform signal is computed using a weighted averaging scheme, the weighted averaging scheme comprising at least one weight variable.

3. The method of claim 2, wherein the at least one weight variable is chosen based at least in part on a signal condition.

4. The method of claim 1, wherein the archetype transform signal is derived at each scale of interest.

5. The method of claim 1, wherein the archetype transform signal is derived continuously over a range of scales.

6. The method of claim 1, further comprising:
using the pulse oximetry system to perform operations comprising:
generating an archetype scalogram based at least in part on the archetype transform signal; and
deriving information about the signal from the archetype scalogram.

7. The method of claim 1, further comprising:
using the pulse oximetry system to perform operations comprising generating a first scalogram based at least in part on the transform signal.

8. The method of claim 1, wherein the physiological parameter comprises pulse rate and/or oxygen saturation and/or a combination thereof.

9. The method of claim 1, further comprising generating an alarm when the physiological parameter is not within a predetermined range.

10. The system of claim 1, wherein the specialized processing hardware and software is further capable of generating an alarm when the physiological parameter is not within a predetermined range.

11. A system for processing a signal, comprising:
a pulse oximetry system, comprising:
a sensor comprising at least one emitter and at least one detector;
a receiver that receives a photoplethysmograph (PPG) signal from the sensor;
specialized processing hardware and software for:
transforming the PPG signal using a continuous wavelet transform to generate a transformed signal, wherein the continuous wavelet transform is based at least in part on a wavelet function;
computing an archetype transformed signal by averaging the transformed signal, wherein the averaging comprises averaging points of the transformed signal with points spaced apart in time, and wherein the spacing is set to correspond to the natural period of the wavelet function used to generate the points of the transformed signal; and
deriving a physiological parameter of a subject from the archetype transform signal;
memory that stores the physiological parameter; and
a display that displays the physiological parameter.

12. The system of claim 11, wherein the archetype transform signal is computed using a weighted averaging scheme, the weighted averaging scheme comprising at least one weight variable.

13. The system of claim 12, wherein the at least one weight variable is chosen based at least in part on a signal condition.

14. The system of claim 11, wherein the archetype transform signal is derived at each scale of interest.

15. The system of claim 11, wherein the archetype transform signal is derived continuously over a range of scales.

16. The system of claim 11, wherein the specialized processing hardware and software is further capable of:
generating an archetype scalogram based at least in part on the archetype transform signal; and
deriving information about the signal from the archetype scalogram.

17. The system of claim 11, wherein the physiological parameter comprises pulse rate and/or oxygen saturation and/or a combination thereof.

* * * * *